US008457915B2

(12) United States Patent
White et al.

(10) Patent No.: US 8,457,915 B2
(45) Date of Patent: Jun. 4, 2013

(54) SYSTEM AND METHOD TO MEASURE THE TRANSIT TIME POSITION(S) OF PULSES IN TIME DOMAIN DATA

(75) Inventors: Jeffrey S. White, Manchester, MI (US); Gregory D. Fichter, Ann Arbor, MI (US); David Zimdars, Ann Arbor, MI (US); Steven Williamson, Ann Arbor, MI (US)

(73) Assignee: Picometrix, LLC, Ann Arbor, MI (US)

( * ) Notice: Subject to any disclaimer, the term of this patent is extended or adjusted under 35 U.S.C. 154(b) by 326 days.

(21) Appl. No.: 12/667,986

(22) PCT Filed: Jul. 14, 2008

(86) PCT No.: PCT/US2008/069935
§ 371 (c)(1),
(2), (4) Date: Jul. 21, 2010

(87) PCT Pub. No.: WO2009/009785
PCT Pub. Date: Jan. 15, 2009

(65) Prior Publication Data
US 2010/0280779 A1   Nov. 4, 2010

Related U.S. Application Data

(60) Provisional application No. 60/959,196, filed on Jul. 12, 2007, provisional application No. 60/959,883, filed on Jul. 17, 2007.

(51) Int. Cl.
*G06F 19/00* (2011.01)

(52) U.S. Cl.
USPC .... 702/79; 250/338.1; 250/341.1; 250/341.3; 250/341.8

(58) Field of Classification Search
USPC ................ 702/79; 250/282, 286, 287, 288, 250/493.1, 495.1, 504 R, 338.1; 356/27, 356/630, 301
See application file for complete search history.

(56) References Cited

U.S. PATENT DOCUMENTS

| | | | |
|---|---|---|---|
| 7,326,930 B2 * | 2/2008 | Crawely | 250/341.1 |
| 7,449,695 B2 * | 11/2008 | Zimdars et al. | 250/341.8 |
| 7,488,940 B2 * | 2/2009 | Ohtake et al. | 250/341.3 |

(Continued)

FOREIGN PATENT DOCUMENTS

| | | |
|---|---|---|
| EP | 1 469 298 A1 | 12/2002 |
| EP | 1 876 438 A1 | 1/2008 |

(Continued)

OTHER PUBLICATIONS

European Search Report and Search Opinion dated Jun. 30, 2010.

(Continued)

*Primary Examiner* — Carol Tsai
(74) *Attorney, Agent, or Firm* — Brinks Hofer Gilson & Lione

(57) ABSTRACT

A system and method to measure, with increased precision, the transit time position(s) of pulses in a time domain data. An example data set would be the transit time of pulses in Time-Domain Terahertz (TD-THz) data. The precision of the pulse timing directly affects the precision of determined sample properties measurements (e.g., thickness). Additionally, an internal calibration etalon structure and algorithm method provides for continuous system precision/accuracy check method to increase sample measurement integrity. The etalon structure can improve the precision of sample property measurements (e.g., absolute thickness). Various hardware and system implementations of the above are described.

27 Claims, 23 Drawing Sheets

U.S. PATENT DOCUMENTS

| | | | |
|---|---|---|---|
| 7,949,019 B2 * | 5/2011 | Bouma et al. | 372/20 |
| 8,129,683 B2 * | 3/2012 | Itsuji et al. | 250/341.1 |
| 2003/0035120 A1 * | 2/2003 | Myatt et al. | 356/519 |
| 2005/0156110 A1 * | 7/2005 | Crawely | 250/338.1 |
| 2006/0244629 A1 | 11/2006 | Miyazaki et al. | |
| 2007/0090294 A1 * | 4/2007 | Safai et al. | 250/341.8 |
| 2007/0235658 A1 * | 10/2007 | Zimdars et al. | 250/390.07 |
| 2008/0265165 A1 * | 10/2008 | Yeh et al. | 250/341.1 |
| 2009/0225313 A1 * | 9/2009 | Umetsu | 356/326 |
| 2009/0251767 A1 * | 10/2009 | Ikari et al. | 359/330 |
| 2011/0222563 A1 * | 9/2011 | Bouma et al. | 372/20 |

FOREIGN PATENT DOCUMENTS

| | | |
|---|---|---|
| GB | 2 446 026 A | 7/2008 |
| GB | 2 446 026 A8 | 7/2008 |
| JP | 2004028618 | 1/2004 |
| WO | WO 2008/135781 A1 | 11/2008 |
| WO | WO 2010/044193 A1 | 4/2010 |

OTHER PUBLICATIONS

Kwang-Su Lee, et al., "The measurement of the dielectric and optical properties of nano thin films by THz differential time-domain spectroscopy," Microelectronics Journal, 34, 63-69, 2003.

Ole Hirsch, et al., "Techniques for cancellation of interfering multiple reflections in terahertz time-domain measurements," Microelectronics Journal, 39, 841-848, 2008.

* cited by examiner

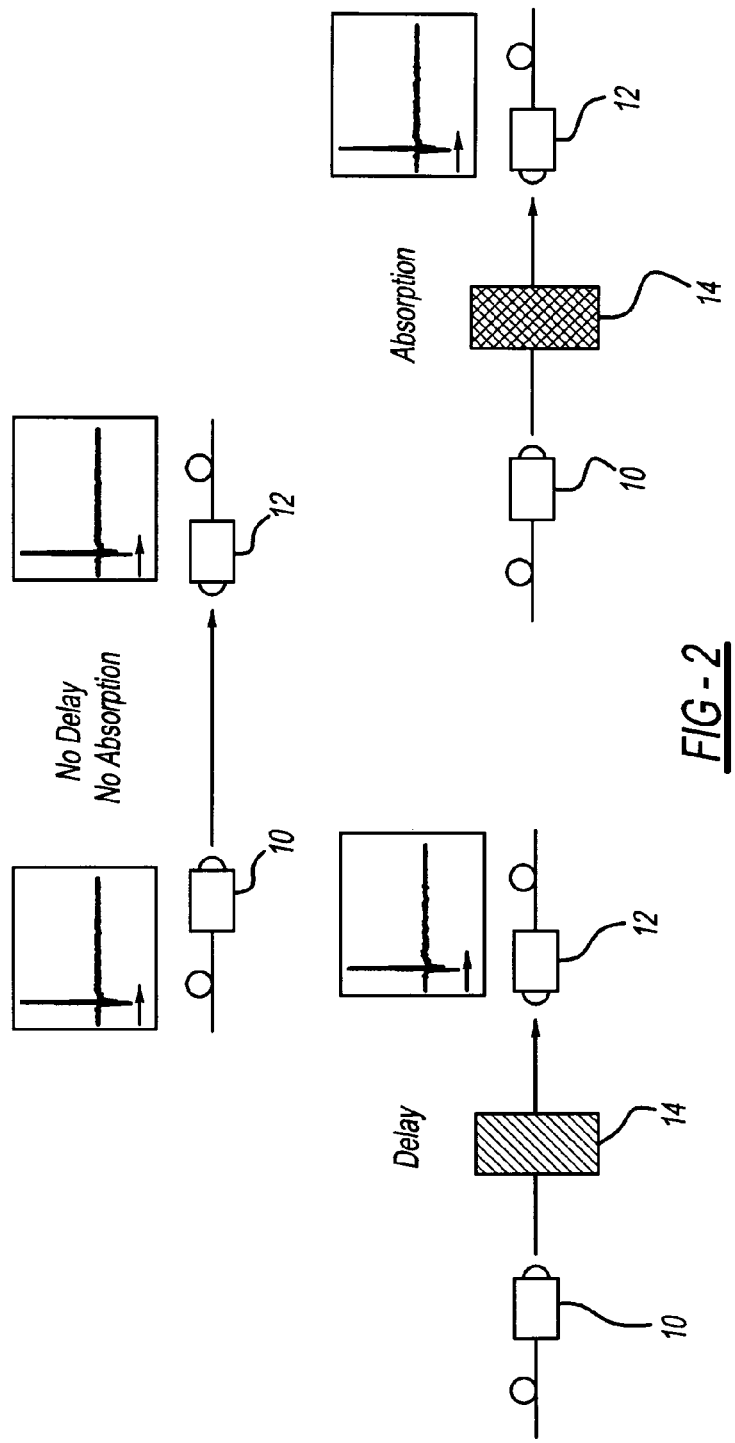

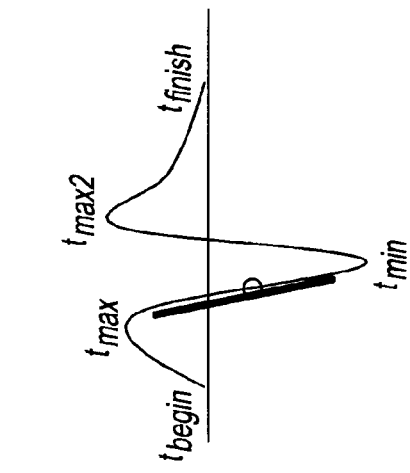
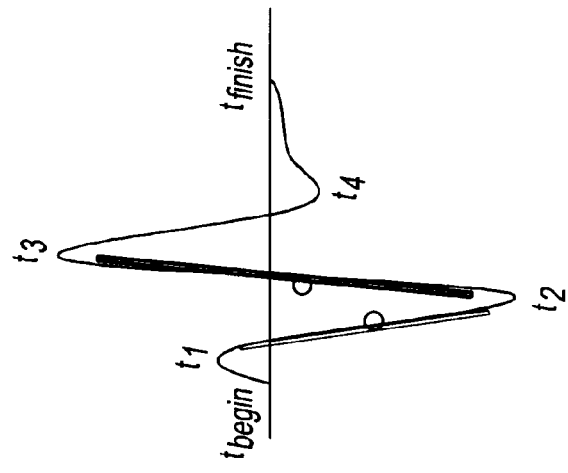
FIG - 13
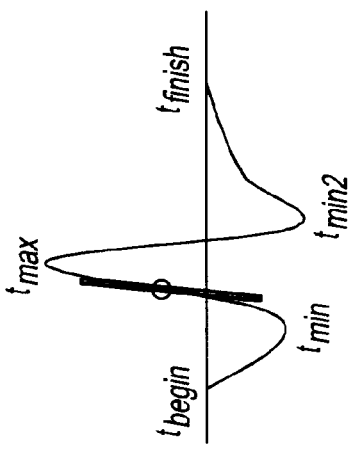
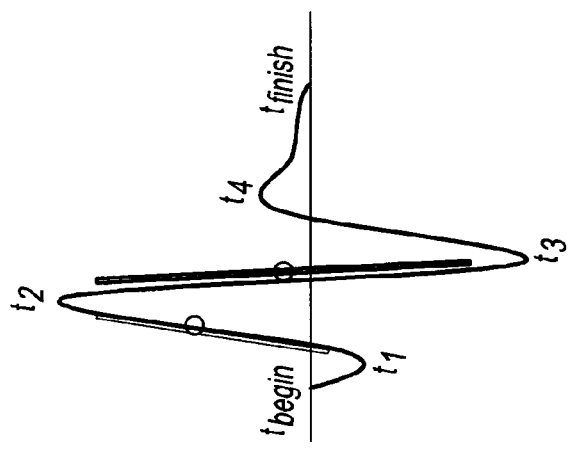
FIG - 14

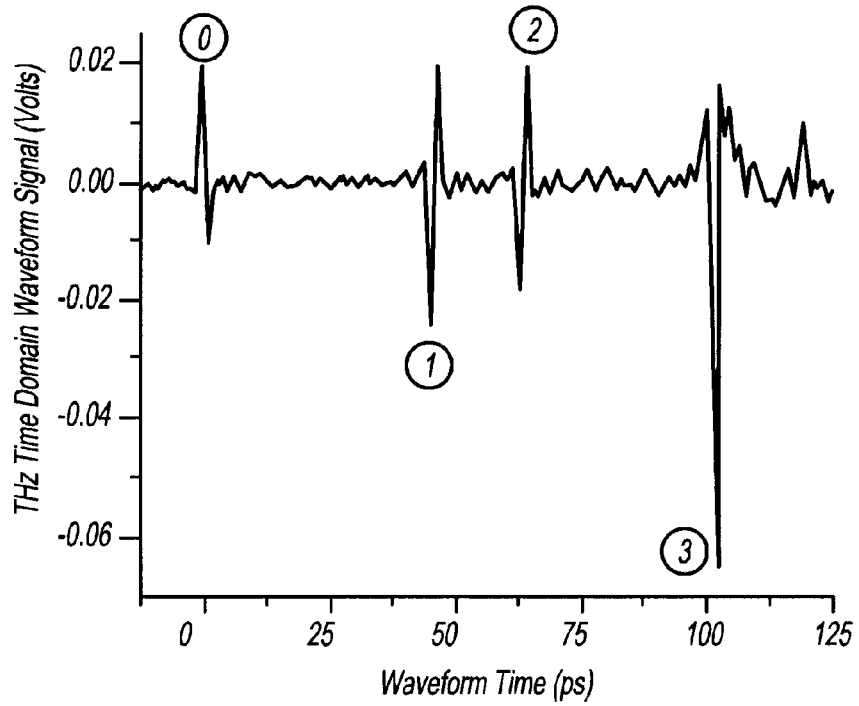
*FIG - 35*
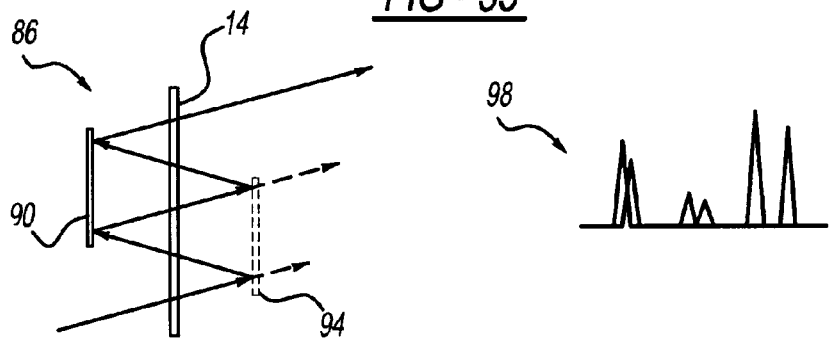
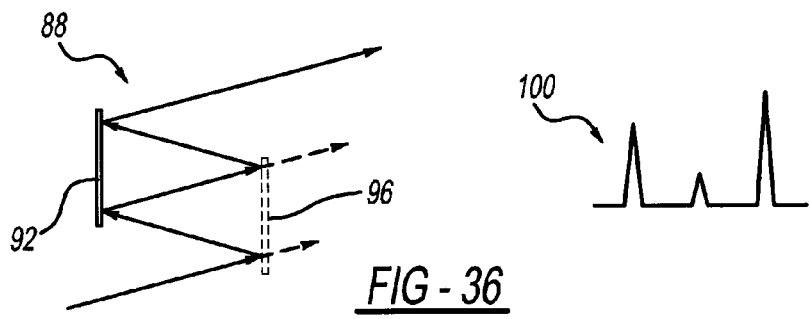
*FIG - 36*

SYSTEM AND METHOD TO MEASURE THE TRANSIT TIME POSITION(S) OF PULSES IN TIME DOMAIN DATA

CROSS REFERENCE TO RELATED APPLICATION

This application claims priority to PCT Application No. PCT/US2008/069935, filed on Jul. 14, 2008, which claims priority to U.S. Provisional Application 60/959,196, filed on Jul. 12, 2007 and U.S. Provisional Application 60/959,883, filed on Jul. 17, 2007, the entirety of which is herein incorporated by reference.

BACKGROUND OF THE INVENTION

The present invention relates to methods to measure the transit time values for pulses in time domain waveform data. Examples will be presented using Time-Domain Terahertz data to determine sample properties. Terahertz electromagnetic radiation is potentially useful in many industrial measurement applications. In TD-THz, essentially single cycle pulses (approximately 1 ps width, FIG. 1) of radiation are synchronously generated and detected. This synchronous method results in high fidelity measurement of the radiation's electric field strength over a waveform time window. This width of this window can vary over a wide range depending on the instrumentation used. As THz radiation pulses are very brief in time, they will contain an extremely wide band of frequencies (10 GHz up to 50 THz).

Once a TD-THz pulse has interacted with a sample, a number of useful measurements can be extracted from acquired time-domain data. Possible measurements include, but are not limited to, sample mass, thickness, density, refractive index, density and surface variations, and spectroscopy (e.g. moisture content, polymorph identification). In FIG. 2 illustrates a terahertz transmitter 10 and terahertz receiver 12. TD-THz, the changes in the THz pulses after they have interacted with material are recorded in a time-domain waveform. For example, as the pulse transmits through a sample 14, the pulse's arrival at the receiver will attenuated and delayed compared to the transmission of the same pulse through an air path (FIG. 2). The amount of the pulse delay is determined by the material's group refractive index value and the amount of mass in the sample beam. The attenuation of the pulse is also dependent on material's refractive index (Fresnel reflection loss), the scattering of radiation with the sample and the attenuation of the pulse's frequencies by the material.

In the top schematic, a THz pulse travels through air with minimum time-of-flight and no loss in amplitude. The addition of essentially transparent solid materials (e.g., plastics, paper, and cloth), in the THz beam path (lower left) will result in a longer time-of-flight for the pulse. The increased time-of-flight will be proportional to the mass and index of refraction of the material. In the bottom right schematic, scattering or absorbing media (such as foam or water laden cloth) will reduce the pulse amplitude in addition to generating a time-of-flight pulse delay.

Many measurements can be made with reflections of the TD-THz pulses off the sample (FIG. 3). This figure illustrates a subset of possible interactions and thus sample properties that can be measured. The consistent need for all measurements is the precision determination of the transit time value for the TD-THz pulse(s).

An example measurement would be sample thickness measurement. This measurement could be made in either transmission or reflection optical geometries. In transmission, the delay of the THz pulse by the sample 14 can be used to measure thickness (FIG. 4). In FIG. 4, Line 16 represents no sample. Line 18 represents a thin sample. Line 20 represents a thick sample. This method requires determining the time position of peaks from two time-domain waveforms that were acquired at two different times (i.e., sample in and out of the beam). This method can result in offset or scaling errors if the position of either peak is shifted due to instrumental or environmental conditions.

Alternatively, THz pulses will reflect some energy at any interface (e.g., Fresnel reflection). Referring to FIG. 5, a multipass sample chamber 21 is illustrated. Reflections using mirrors 22 and 24 from the front and rear surface of a sample can be observed as shown in FIG. 6. The time delay between these two reflection peaks is determined by the mass and the refractive index of the material. Thus, it is possible to measure the sample's mass, thickness and/or density of a sample from a single time-domain waveform. Measurements made in this manner will exhibit reduced offset or timing slope errors.

Multipassing the THz pulses through the sample would increase the observed time delay without changing the imprecision of the pulse time measurement (as long a sufficient Signal-to-Noise is maintained). This concept is illustrated in FIG. 4. This method would increase the overall sample thickness measurement precision.

An interesting aspect of reflection waveforms is the polarity of the waveform pulses. TD-THz measures the direct electric field, thus the polarity of the pulse does indicate the electric field polarity. In transmission measurements, the presence of a sample does not affect the pulse polarity. However, for reflection measurements, the pulse will flip polarity when reflecting off a low to high refractive index or metal interface. That is why the first pulse in the reflection waveform of FIG. 6 (air-to-sample) is flipped in polarity. The strength of reflection is dependent, among other factors, on the difference in refractive index between the two materials. This information can be used to determine the delta refractive index change, including the sign of the delta, of the two materials across the interface.

BRIEF DESCRIPTION OF THE DRAWINGS

FIG. 2 illustrates a THz pulse interactions with materials;

FIG. 13 illustrates two standard cases for multiple peak find;

FIG. 14 illustrates two non-standard 'bipolar' cases for multiple peak find;

FIG. 35 illustrates a TD-THz waveform for sample in Internal Calibration Etalon/Rear Reflector structure;

FIG. 36 illustrates a sample multipass etalon;

DETAILED DESCRIPTION OF THE INVENTION

In order to make a number of different sample property measurements, the transit time of the TD-THz pulse(s) needs to be precisely determined. This can be accomplished with multiple methods. Three algorithms for rapid, high precision pulse time value, using TD-THz pulses as example data, are presented; edge midpoint method, model fitting method, and a deconvolution with fitting method. Guidelines for determining the best algorithm are described below.

Figure 7:
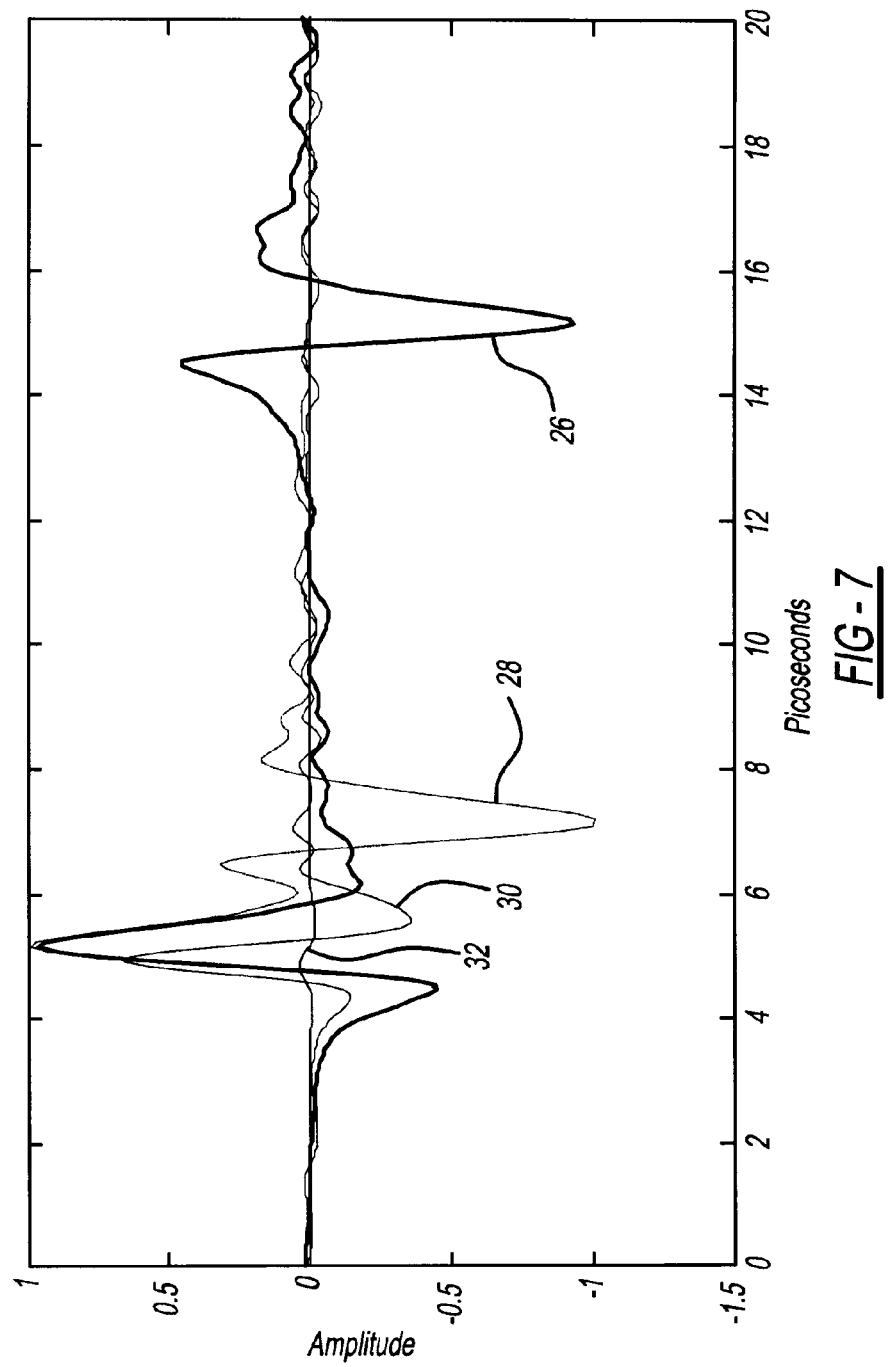
FIG. 7 illustrates a simulated example of a TD-THz pulse reflected from various material thicknesses.
Figure 8:
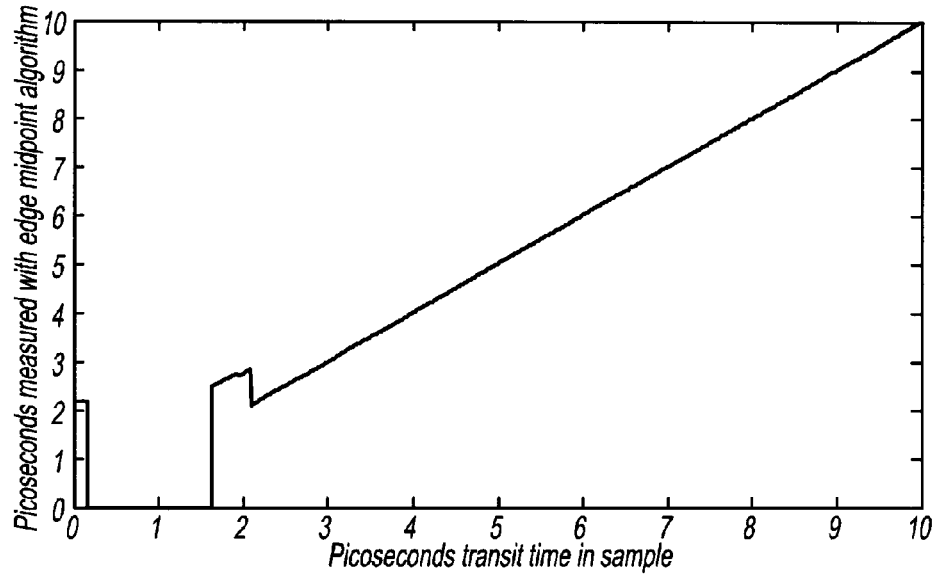
FIG. 8 illustrates a plot of the edge midpoint algorithm applied to various sample thicknesses.
Figure 9:
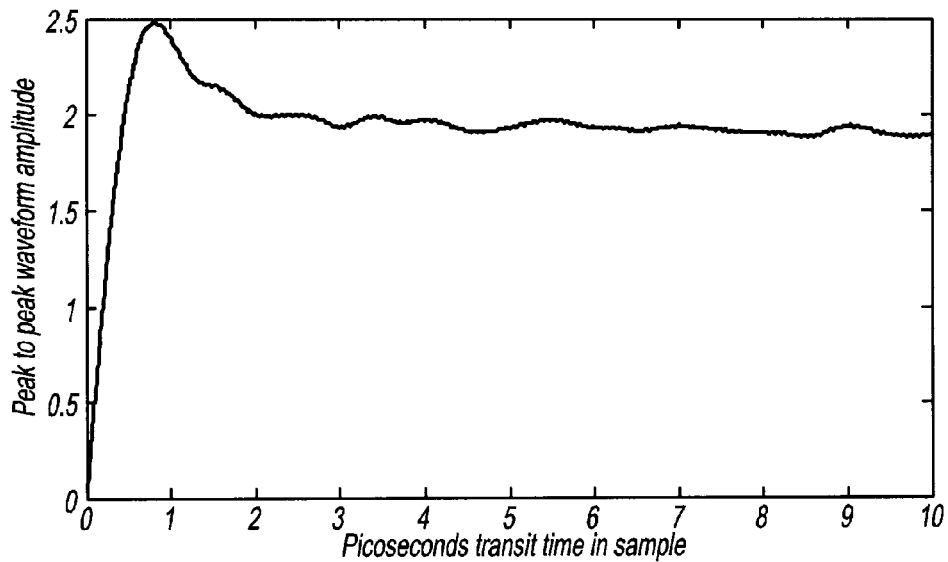
FIG. 9 illustrates a plot of the peak-to-peak reflected waveform amplitude versus sample thickness.

The selection of algorithm depends on multiple factors; FIG. 7 helps illustrate this point. The waveform 26 simulates a 10 ps delay between the front and back reflections, equivalent to 3 mm of n=1.5 material. The waveform 28 is 2 ps (0.6 mm), waveform 30 is 0.02 ps (60 microns), and waveform 32 is 0.005 ps (15 microns). The edge midpoint algorithm is generally a faster computational method, but it typically does not function as well on very thin samples (FIG. 8). The peak-to-peak amplitude method is also fast, but only works on very thin samples (FIG. 9). The model fitting and deconvolution algorithms typically work with all samples, and provides higher precision (Table 1), but are slower to compute.

Figure 10:
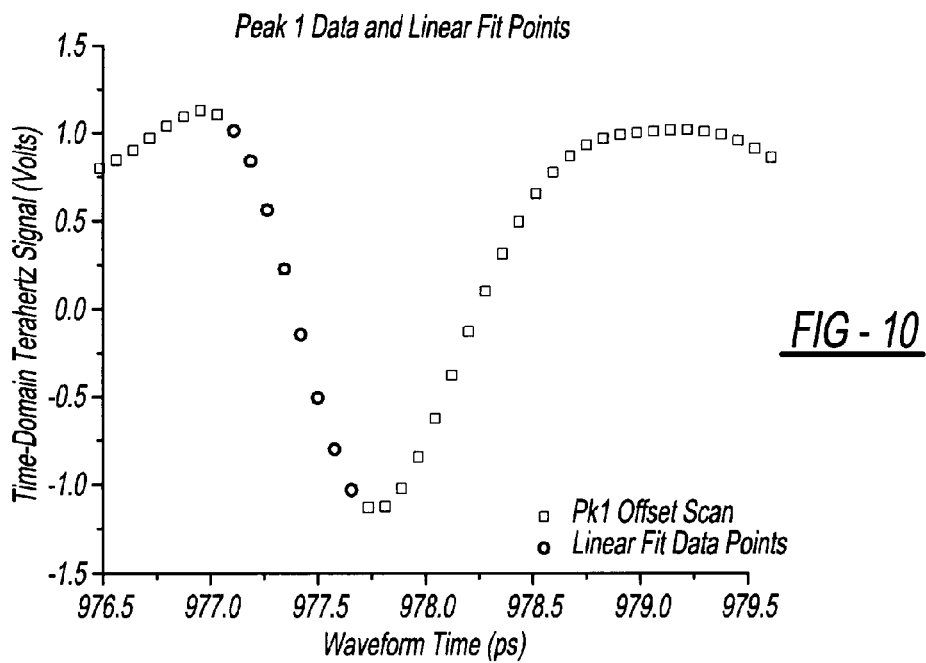
FIG. 10 illustrates a pulse edge for midpoint determination.
Figure 11:
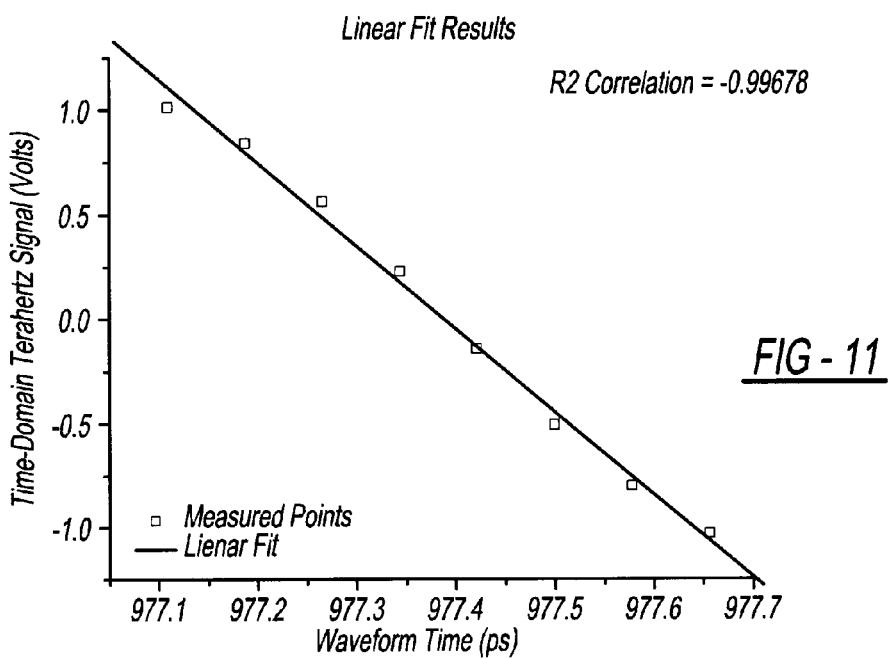
FIG. 11 illustrates a linear fit of selected edge midpoint.

In the edge midpoint method, the midpoint of a pulse's edges are determined and offset so that they are at 0V. A number of points around the 0V midpoint are selected for analysis (FIG. 10). Then a linear fit of the data is performed for points around this midpoint (FIG. 10). The resulting linear fit equation is solved for its intercept and that value is the time assigned to that peak. This method is computationally simple and provides high precision of the peak time position, on the order of 1/5th of the waveform measurement point spacing, a significant improvement in timing precision.

A linear fit of the selected points provides the most computationally simple and thus fastest method to precisely determine the edge midpoint. However, higher order fits are also possible and can provide further time precision improvements are achieved. A 3rd order polynomial had demonstrated improved fitting precision. Other non-linear or higher order fits are possible.

Figure 12:
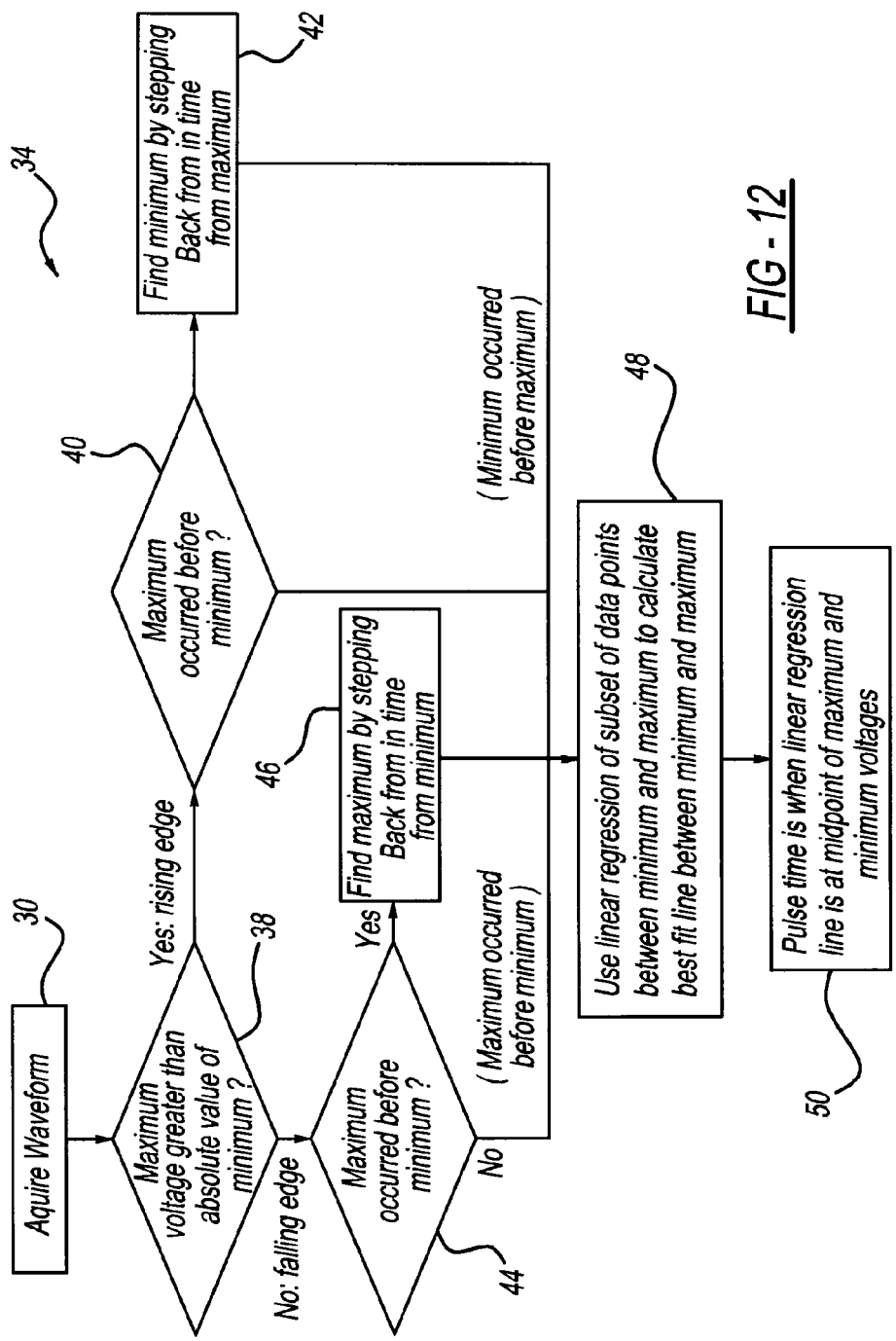
FIG. 12 illustrates a Flowchart for midpoint determination.
Figure 15:
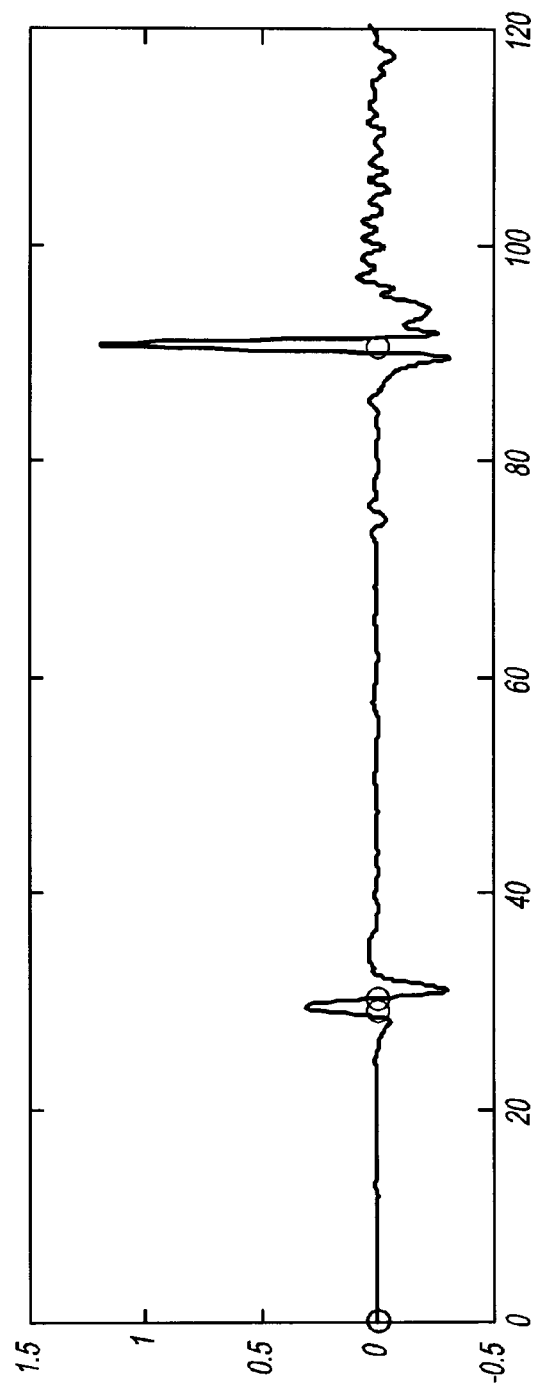
FIG. 15 illustrates a case wherein the first peak is noted as bipolar and the second as a standard type.

A flowchart detailing the method 34 for a midpoint determination is shown in FIG. 12. Example peak shapes are highlighted in FIG. 13, where the two standard cases for multiple peak find. If the ratio of Vmin/Vmax is too large, the peak is assumed to be a bipolar case as given below. If the ratio of Vmin/Vmin2 (or Vmax/Vmax2) is too large, the peak is marked as irregular (type 3).

FIG. 14 provides the two non-standard 'bipolar' cases for multiple peak find. The above results confirm we are able to resolve and quantify multiple peaks and edges per peak using the edge midpoint detection algorithm.

Referring to FIG. 12, the method 34 first acquires a waveform as shown in step 36. In step 38, a determination is made if a maximum voltage is grater than the absolute value of the minimum of the waveform. If step 38 is true, then a determination is made in step 40 if the minimum occurred before the maximum. Thereafter, in step 42, a minimum is found by stepping back from the maximum. The method 34 then continues to step 48 which will be described in grater detail in the paragraphs that follow.

If step 38 is false, a determination is made in step 44 if the maximum occurred before the minimum. If step 44 is false, the method continues to step 48 which will be described in grater detail later. Otherwise, the method continues to step 46 where the maximum is determined by stepping back from the minimum.

In step 48, a linear fit is accomplished by using a linear regression of a subset of data points between a minimum value and a maximum value of the waveform. Finally, in step 50, a pulse time is determined by when the linear regression line is at a midpoint of maximum and minimum voltages.

Figure 16:
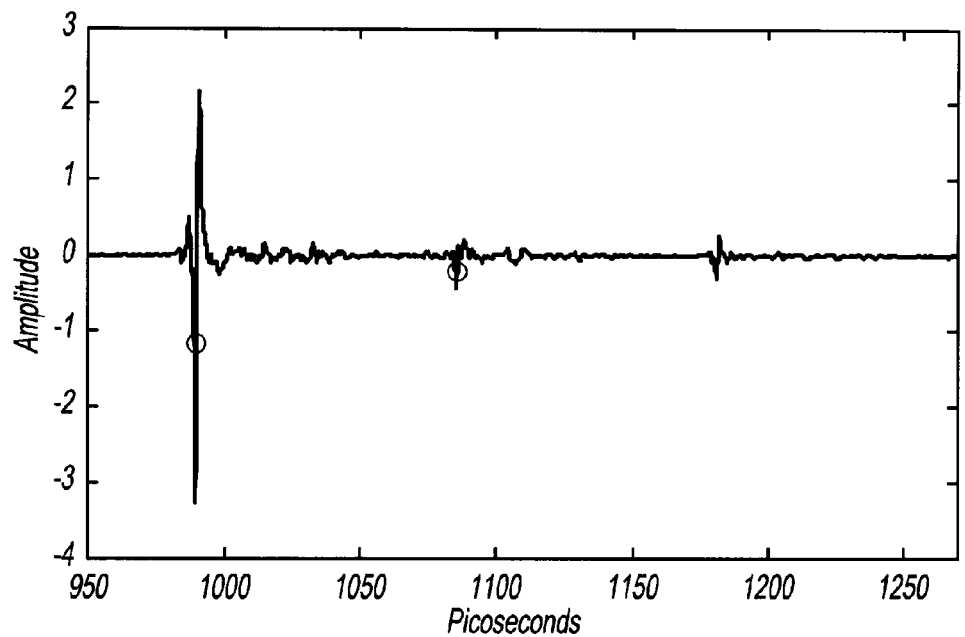
FIG. 16 illustrates a model waveform.
Figure 17:
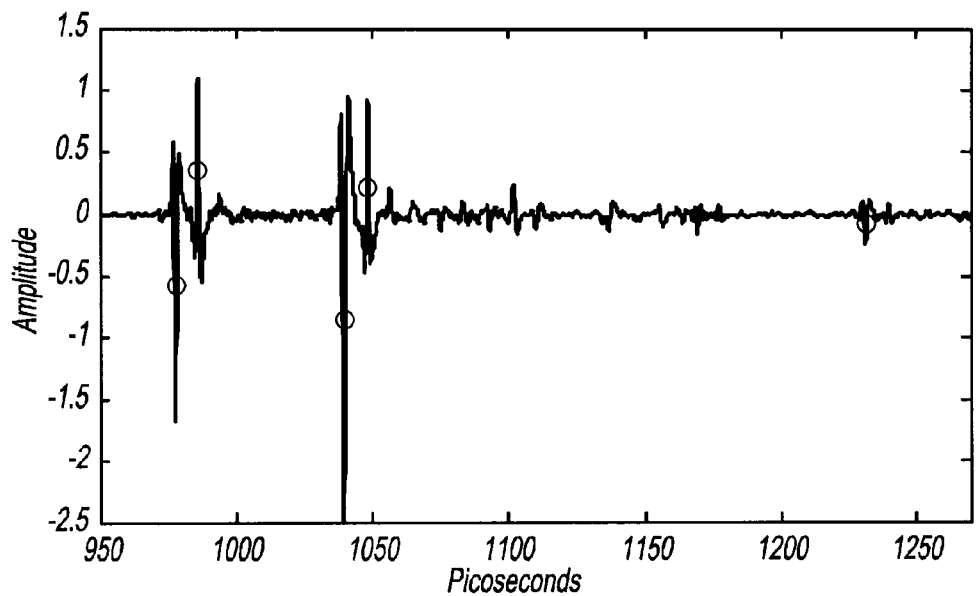
FIG. 17 illustrates a sample waveform, wherein the first two peaks are the plastic shim, and the second two peaks are a silicon reference etalon.
Figure 18:
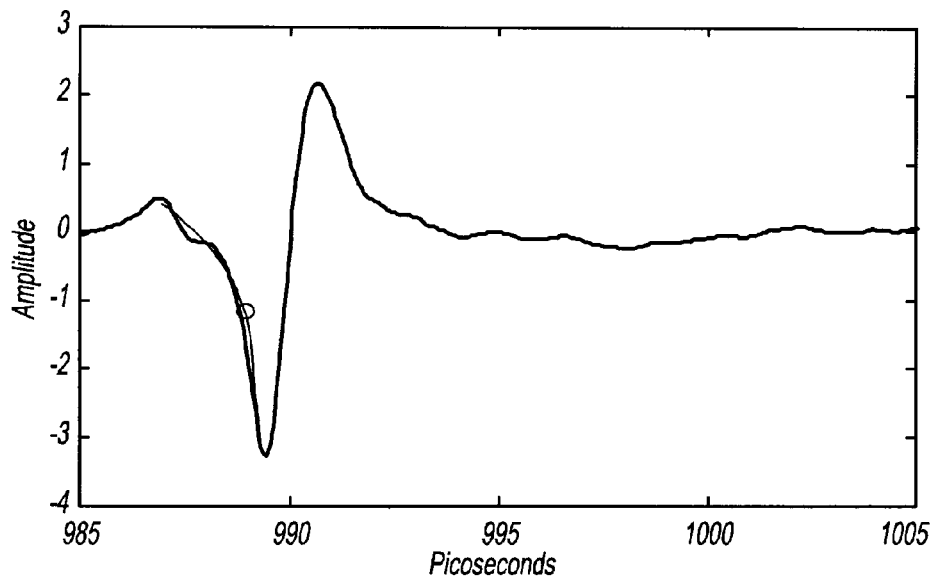
FIG. 18 illustrates a zoomed view of model waveform peak.
Figure 19:
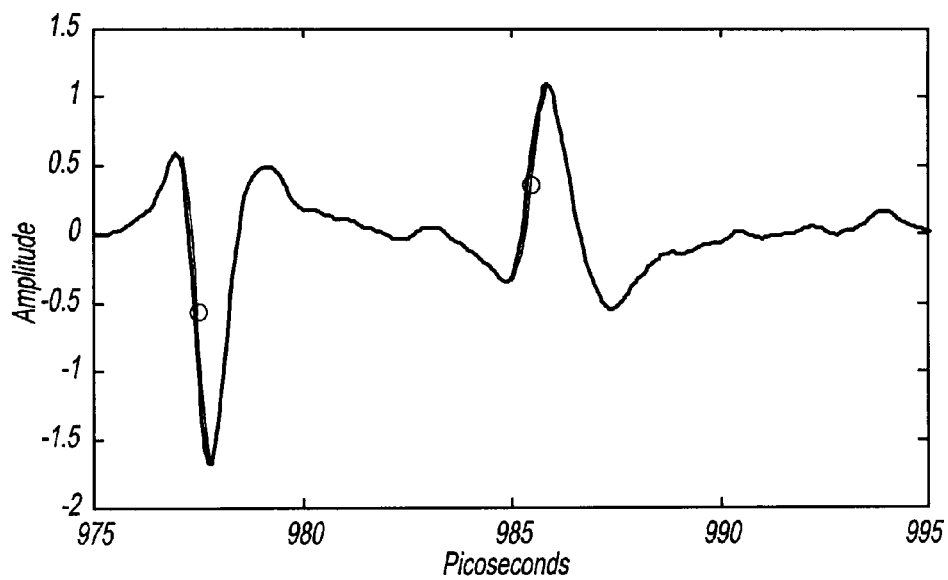
FIG. 19 illustrates a zoomed view of sample waveform peaks.
Figure 20:
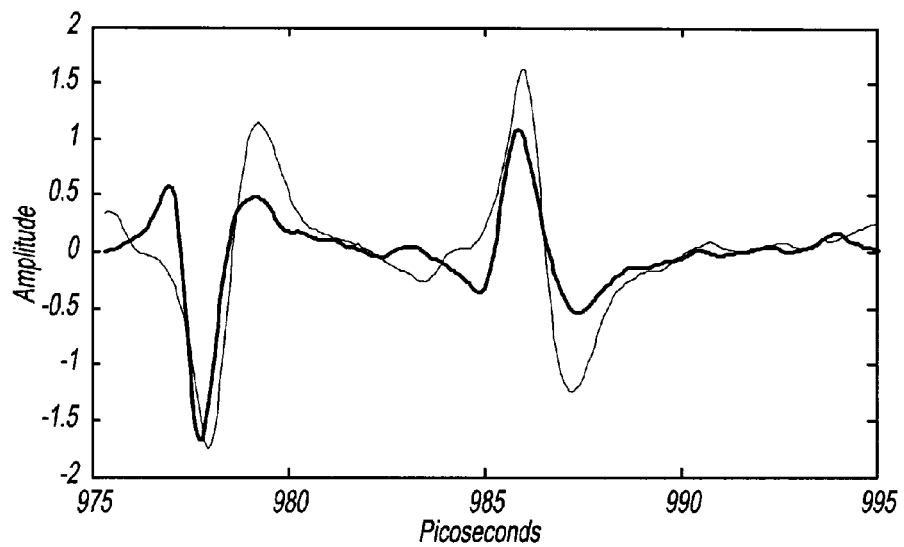
FIG. 20 illustrates a starting point of trial fit of model waveform to sample waveform using 256 points.
Figure 21:
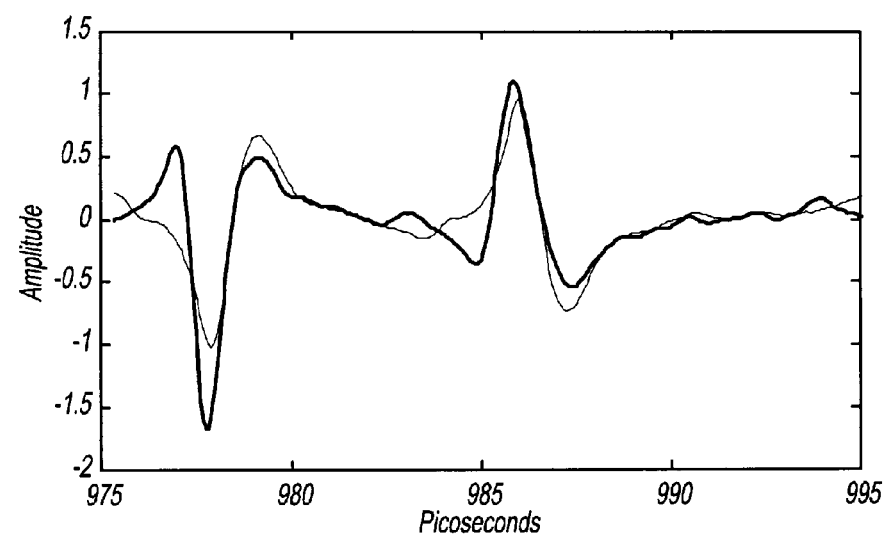
FIG. 21 illustrates a final result after method optimization.

This model fitting method uses the edge midpoint method as a starting point for fitting a model waveform. The model waveform is a single THz pulse (FIG. 16, FIG. 18), collected as much as possible using the same conditions as the sample waveform (FIG. 17, FIG. 19). The edge midpoint is used to generate a starting point for the model fitting, which then uses a simplex optimization method to evaluate a series of trial waveforms with varying timing and amplitude and converge on the best solution parameters For initial testing, two copies of the model waveform are used to fit the front and back of a 0.02" thick plastic shim. In FIG. 20, waveform 52 is sample waveform, and waveform 54 is trial waveform, wherein the starting point of trial fit of model waveform to sample waveform using 256 points. FIG. 21 illustrates the final result after method optimization, wherein waveform 56 is sample waveform, and waveform 58 is trial waveform. The optimization varies the timing of the two copies and overall scaling of the waveform. The timing $\Delta_T$ is varied by changing the phase of the Fourier transform, $$\phi(\upsilon)=2\pi(\Delta\tau)\upsilon$$

because this frequency domain method gives precise results without interpolation. The trial waveform is generated from the model waveform by $$W_{trial}=C*FFT^{-1}(FFT(W_{ref})e^{i\phi(\upsilon)}(1-e^{i\delta(\upsilon)}))$$

where $W_{trial}$ and $W_{ref}$ are the time domain trial and reference waveforms, C is a scaling factor, $\phi(v)$ is the phase shift from the model peak to the first sample peak, and $\delta(v)$ is the phase shift from the first sample peak to the second sample peak. The optimization tries to minimize the RMS value of the difference between the trial and sample waveforms $$Err = \sqrt{\langle(W_{sample}(\tau) - W_{trial}(\tau))^2\rangle}$$

The initial results are that this method is consistently slightly better than the zero crossing method, even when the model waveform is not optimal:

TABLE 1

Results of peak fitting 100 waveforms collected using the spinner. Each waveform itself is 99 averages. The time is measured on a slow Personal Computer.

| Method | Standard deviation (mean 8 to 8.15 ps) | Time required |
|---|---|---|
| Zero crossing method | 1.62 fs | 0.046 sec |
| Peak fitting, 256 points | 0.91 fs | 0.21 sec |
| Peak fitting, 512 points | 0.90 fs | 0.33 sec |
| Peak fitting, entire waveform | 0.91 fs | 2.80 sec |

For the deconvolution method, THz measurements can be considered as the convolution of the inherent instrument response (due to photoconductive material properties, laser pulse shape, transmitter and receiver antenna geometries, etc.) with the surface(s) of the sample. If the instrument response can be determined separately, for instance by using a reference surface, the THz measurement can be deconvolved to extract the sample surface data alone. Deconvolution has been reported in the past for THz 3D reconstruction. The unique element here is the application of deconvolution to thickness measurements. Deconvolution prior to model fitting improves the accuracy of the results.

The convolution of two functions is equivalent to multiplication of their Fourier transforms:

$$y(t) = x(t) * h(t) \equiv \int_{-\infty}^{\infty} x(\tau)h(t-\tau)d\tau$$
$$y(t) = \mathcal{F}^{-1}(\mathcal{F}(x(t))\mathcal{F}(y(t)))$$

For THz signals the acquired terahertz waveform y(t) is the convolution of the reference waveform or instrument response h(t), with the Fresnel reflections from the actual object x(t). The object may have multiple layers of differing refractive index, absorbance and thickness. $\mathcal{F}(x)$ and $\mathcal{F}^{-1}(t)$ represent the forward and inverse Fourier transforms respectively.

Deconvolution is the inverse operation of reconstructing an unknown object given the acquired THz waveform and a THz reference waveform. The simplest method of deconvolution uses a division in the Fourier domain:

$$x(t) = \mathcal{F}^{-1}\left(\frac{\mathcal{F}(y(t))}{\mathcal{F}(h(t))}\right)$$

This division produces very noisy results because the THz measurement is oversampled to prevent aliasing. The oversampled measurement has zero or minimal SNR over part of the frequency range, and in this frequency range the result of the division is to amplify the noise. The solution is to filter the measurement. One method is a simple bandpass filter. However, this needs to be adjusted for the bandwidth of each THz system configuration, and may create impulse response artifacts. An alternate filter R(a) is the Tikhonov filter, a simple, gradual filter to eliminate low-SNR parts of the spectrum:

$$R(\omega) \equiv \frac{1}{1 + \frac{\tau}{|\mathcal{F}(h(t))|^2}}$$

This method is proposed in the context of imaging deconvolution. Doing the filtering and deconvolution simultaneously reduces the number of transforms required:

$$x(t) = \mathcal{F}^{-1}\left(\frac{\mathcal{F}(y(t))}{\mathcal{F}(h(t))}R(\omega)\right)$$
$$x(t) = \mathcal{F}^{-1}\left(\frac{\mathcal{F}(y(t))}{\mathcal{F}(h(t))}\frac{|\mathcal{F}(h(t))|^2}{|\mathcal{F}(h(t))|^2 + \tau}\right)$$
$$x(t) = \mathcal{F}^{-1}\left(\frac{\mathcal{F}(y(t))\mathcal{F}^*(h(t))}{|\mathcal{F}(h(t))|^2 + \tau}\right)$$

Figure 23:
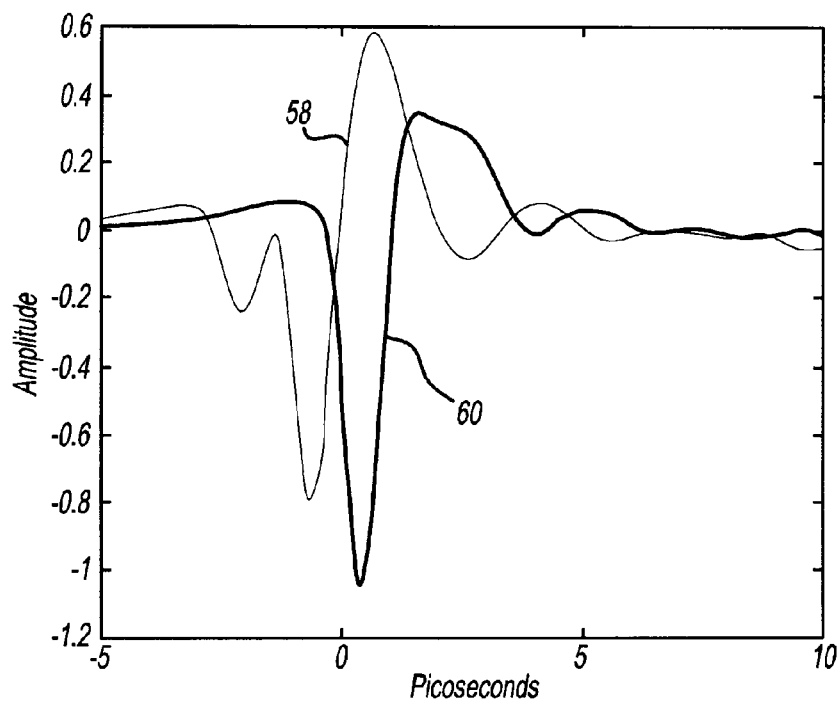
FIG. 23 illustrates sample data for deconvolution method.
Figure 24:
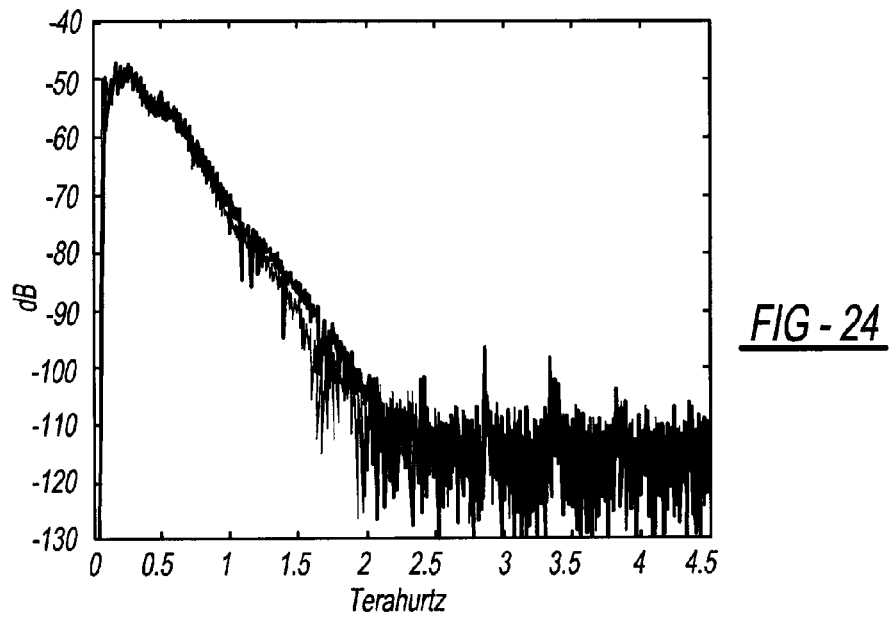
FIG. 24 illustrates a Fourier transform of the data in FIG. 23.
Figure 25:
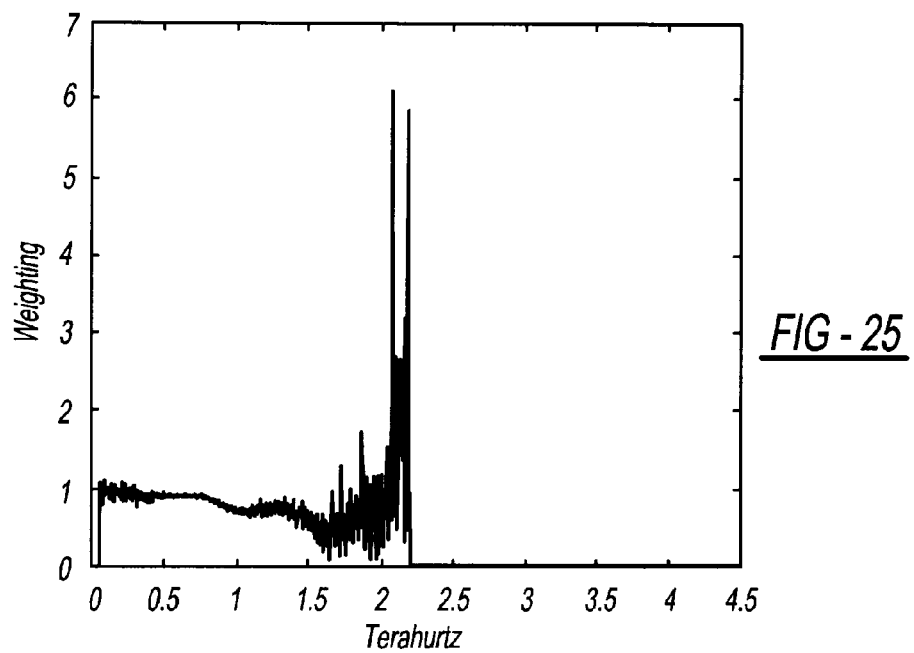
FIG. 25 illustrates a frequency domain result of dividing the sample by the reference.
Figure 26:
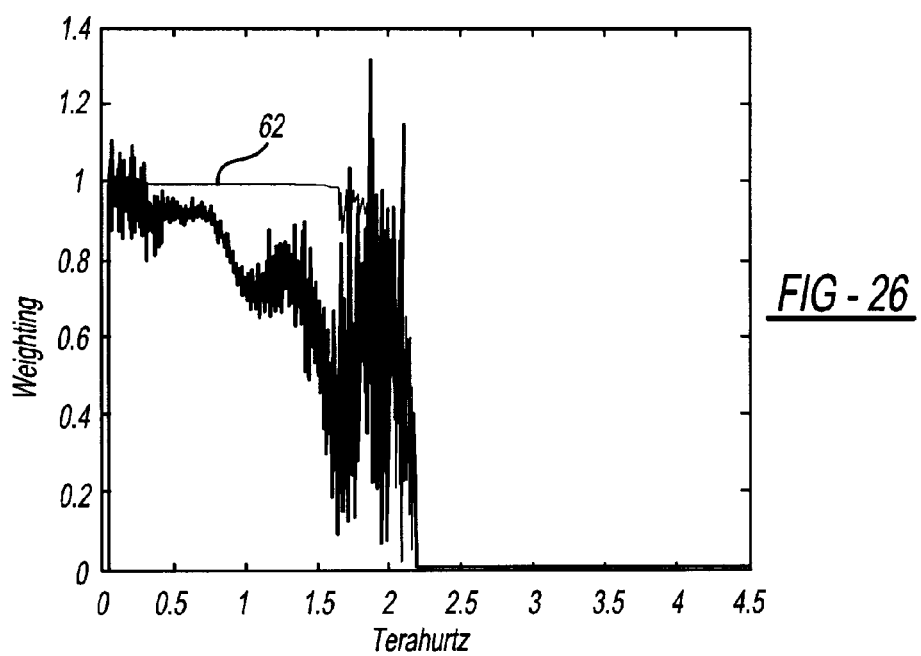
FIG. 26 illustrates a Tikhonov filter to the result of FIG. 25 causes a re-weighting of the data toward the frequencies with greater signal to noise ratio.

FIG. 23 shows a sample THz measurement and reference measurement. The line 58 is a reflected THz measurement from a painted panel. The line 60 is the instrument response, measured separately. FIG. 24 shows the Fourier transforms of the measurements. FIG. 25 and FIG. 26 show the result of the division in the Fourier domain. In FIG. 25, the signal has already been bandpassed to limit it to 2.2 THz. However, the increasing variability of the signal at higher frequencies (e.g. around 0.5 THz vs. around 2 THz) is a result of the SNR variation in the broadband THz pulse. In FIG. 26, the results are shown of applying the Tikhonov filter to the result of FIG. 25 causes a reweighting of the data toward the frequencies with greater SNR. The line 62 is the result of dividing the reference pulse by itself and applying the same filtering.

Figure 27:
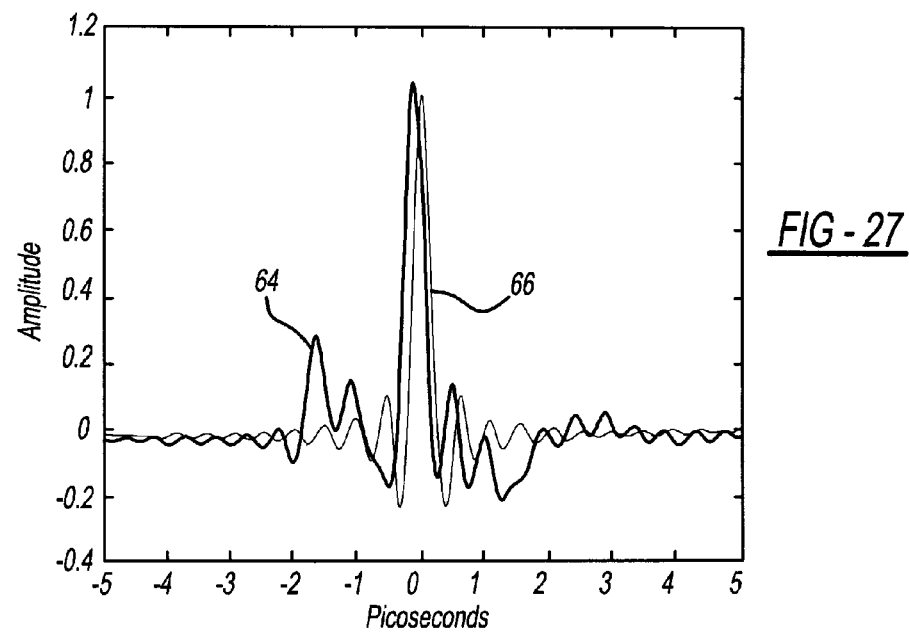
FIG. 27 illustrates an inverse Fourier transform of the data in FIG. 26, which is the completed deconvolution of the data in FIG. 23.

FIG. 27 shows the completed deconvolution. The peaks are narrower and symmetric, which makes them more discernable than the original waveforms. Line 64 is the inverse Fourier transform of the data in FIG. 26, which is the completed deconvolution of the data in FIG. 23. Line 66 is the deconvolution of the reference pulse, which can be fit to the sample pulse for increased accuracy. The deconvolution method is followed by a model fitting. As described above, the timing and amplitude of the fitting function is varied using a simplex multidimensional search technique.

Figure 28:
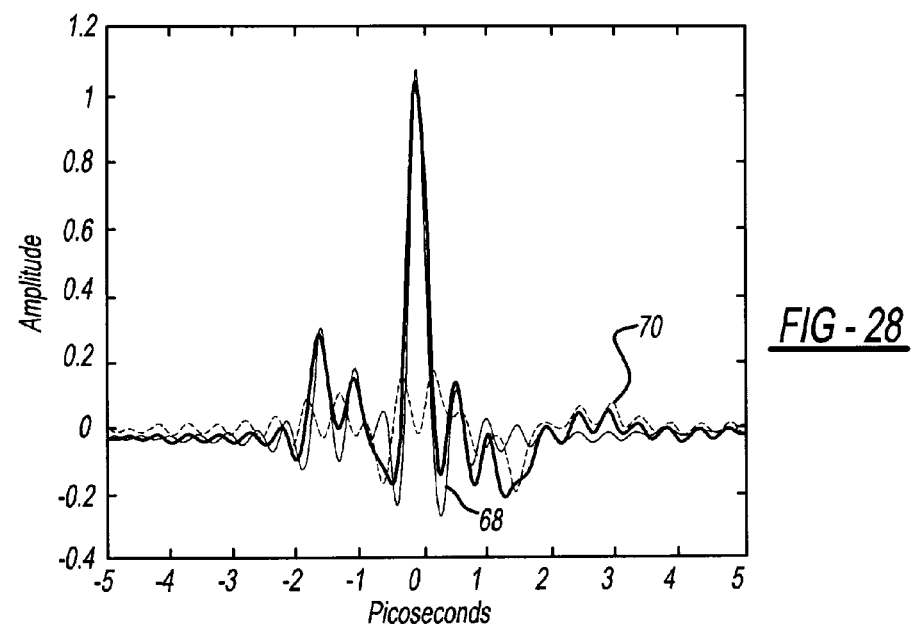
FIG. 28 illustrates a model fitting applied to a deconvolution result.

In FIG. 28, model fitting applied to the deconvolution result. The line 68 is the result of fitting 3 copies of the reference pulse to the sample pulse. Line 70 is the residual error.

Figure 29:
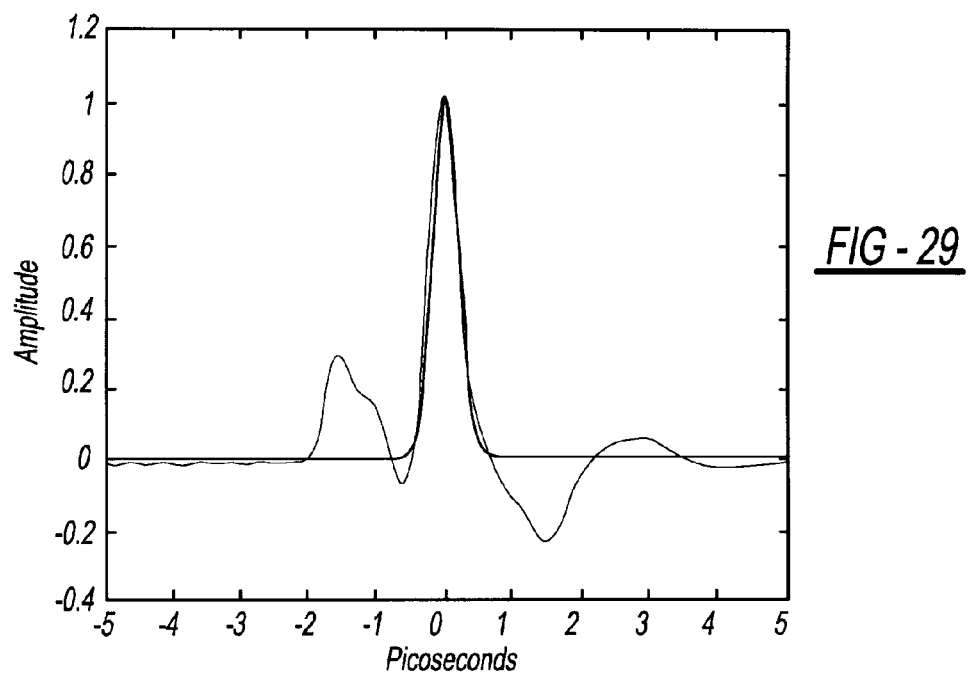
FIG. 29 illustrates a result of convolving FIG. 27 with a Gaussian.
Figure 30:
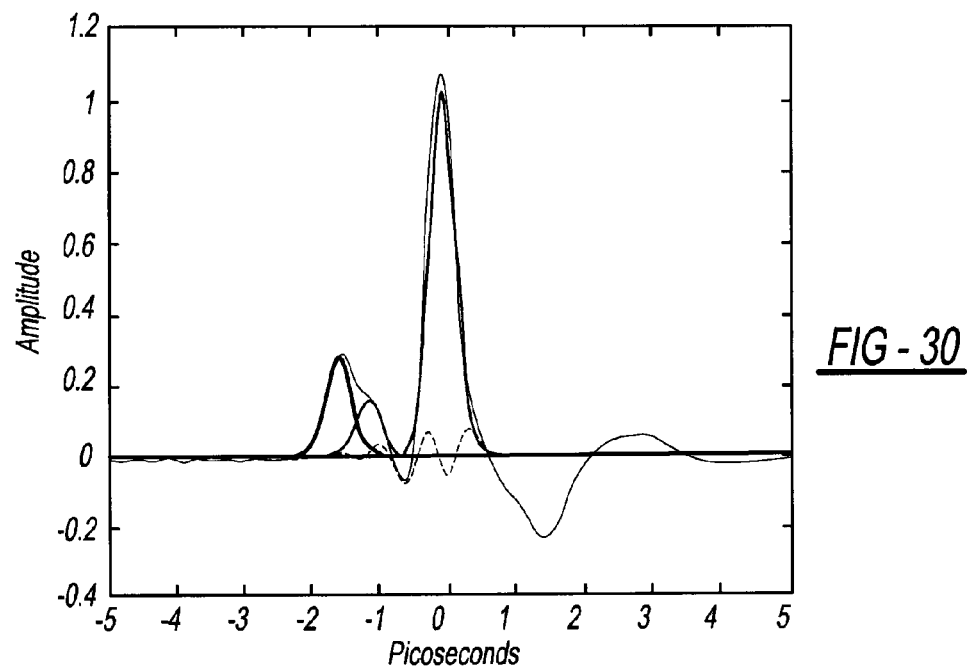
FIG. 30 illustrates a model fitting of FIG. 29.

A further refinement is to convolve the deconvolved result with a smooth, compact function such as a Gaussian, as shown in FIG. 29 and FIG. 30. FIG. 29 is the result of convolving FIG. 27 with a Gaussian. The Gaussian has relatively compact support and minimizes ripple, although the FWHM of the peaks is slightly increased. FIG. 30 is the model fitting of FIG. 29.

Figure 31:
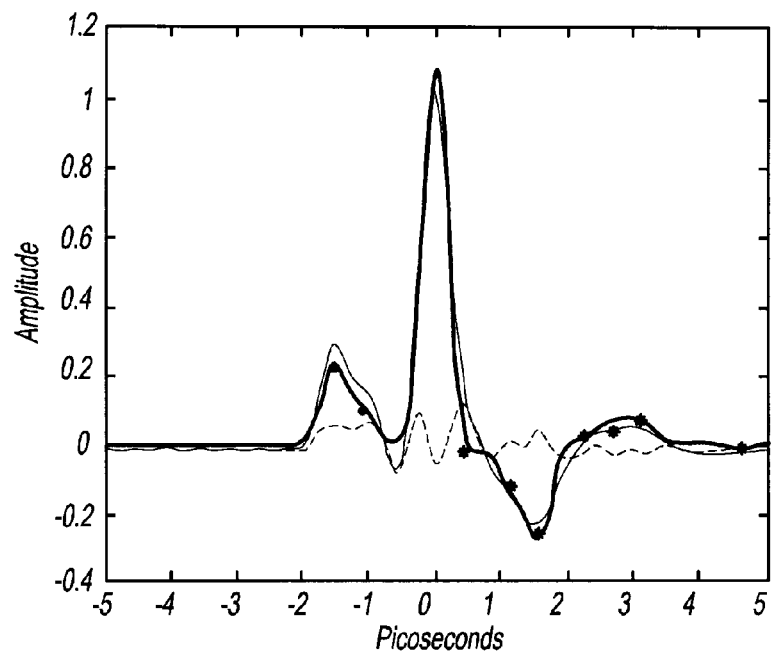
FIG. 31 illustrates a model fitting of FIG. 30 including reflections.

An additional refinement is to use known or assumed refractive index values for the layer materials to calculate the internal reflections within the sample as shown in FIG. 31. The round dots indicate the amplitude and timing of the main reflections, and the stars indicate multiple bounces of the terahertz pulse between paint layers. The dotted line again indicates the residual error.

Figure 22:
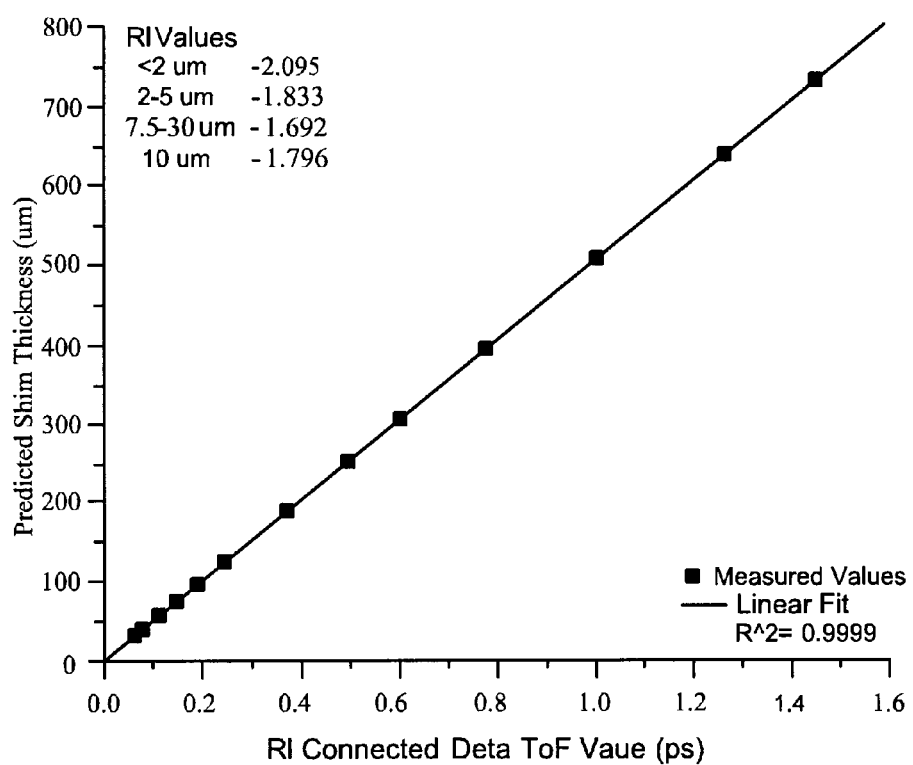
FIG. 22 illustrates a plastic shim thickness measurement results.

A major advantage of the deconvolution/fitting method is the extension to thinner samples the expected linear behavior of the fit of the delta transit time between reflections off the front and rear surfaces of samples to the thickness of the sample (FIG. 22).

As discussed, the primary measurement characteristics of time-domain Terahertz waveform pulses are the pulse's position in time and amplitude. It is well understood that instrumental or environmental conditions (e.g., noise, drift) effect the measurement, in this case decreasing the precision of the peak time position or amplitude measurement. A system internal reference could both confirm proper system operation, and, if necessary, provide data for corrections (e.g., amplitude scaling or time calibration) to the sample waveform results.

Figure 32:
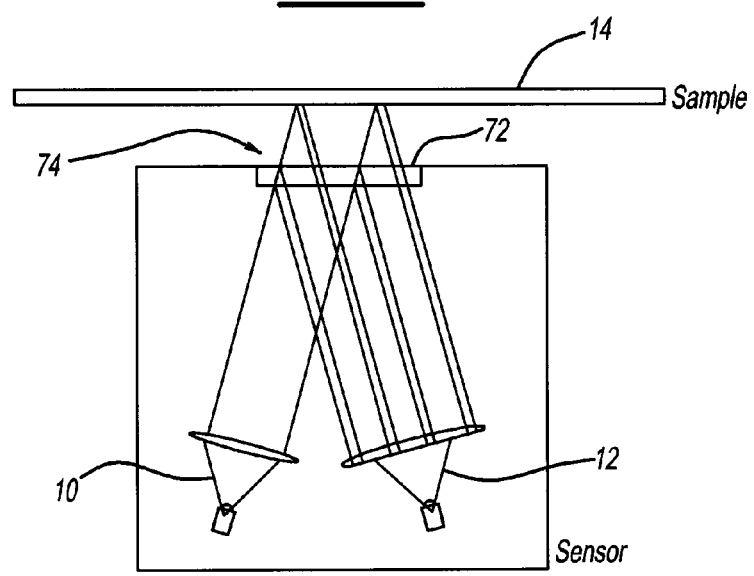
FIG. 32 illustrates a sensor with Internal Calibration Etalon.
Figure 33:
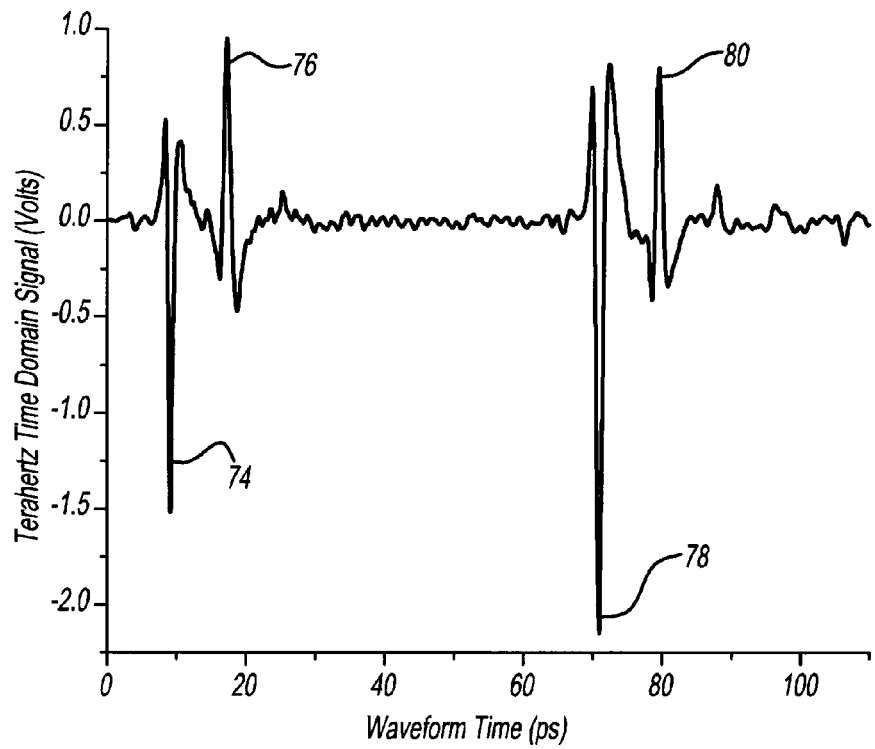
FIG. 33 illustrates a Reflection waveform from Internal Calibration Etalon Sensor and single layer sample.

As previously noted, any refractive index interface will generate a reflection of a THz pulse. As shown in FIG. 32, the proposed invention and implementation here is to install an internal calibration etalon 72 in the sensor head 74 that would provide reflection signals to be used for system and measurement calibration. Note that, for a sensor with this internal calibration etalon and a single layer film type sample shown, four interfaces (etalon front and rear surface and sample front and rear surface) are present. Thus four reflection peaks (designated by the reference numerals 74, 76, 78 and 80 in FIG. 33 are expected. A TD-THz waveform of such an experimental configuration is shown in FIG. 22. The expected 4 reflection peaks are observed.

Also note that this concept is not limited to 4 interfaces, but could be extended to any number of interfaces, for example multilayer samples or stacked samples.

The calibration etalon would be ideally manufactured from a stable material with a low thermal expansion coefficient, low index of refraction at THz frequencies and extremely low absorption. High Density Polyethylene (HDPE) is a reasonable target material. Low resistivity Silicon or fused silica are also options.

The purpose of this calibration etalon would be to provide for a simultaneous measurement of the timing and amplitude of the etalon and the sample for each individual waveform acquisition. Changes in the instrumentation or environmental conditions would be reflected as changes in the calibration etalon peaks. The etalon would be chosen to provide a stable signal, thus changes in the etalon measurements could be used to adjust the sample measurements. Example adjustments would include scaling the sample delta time measurement or using the calibration signal amplitude information to improve the model fit algorithm. It is important to note again that this calibration/reference information would be contained within each individual TD-THz reflection waveform. The TD-THz waveform time window would have to be long enough to ensure both the calibration etalon and sample reflections occur within this window. The previously discussed pulse time position methods and algorithms would be critical to provide sufficient precision to allow this calibration standard to be useful. In addition, the amplitude of the reflected pulses could be used to help model the reflected sample waveform pulses, especially for the peak to peak amplitude and model fitting methods.

Figure 6:
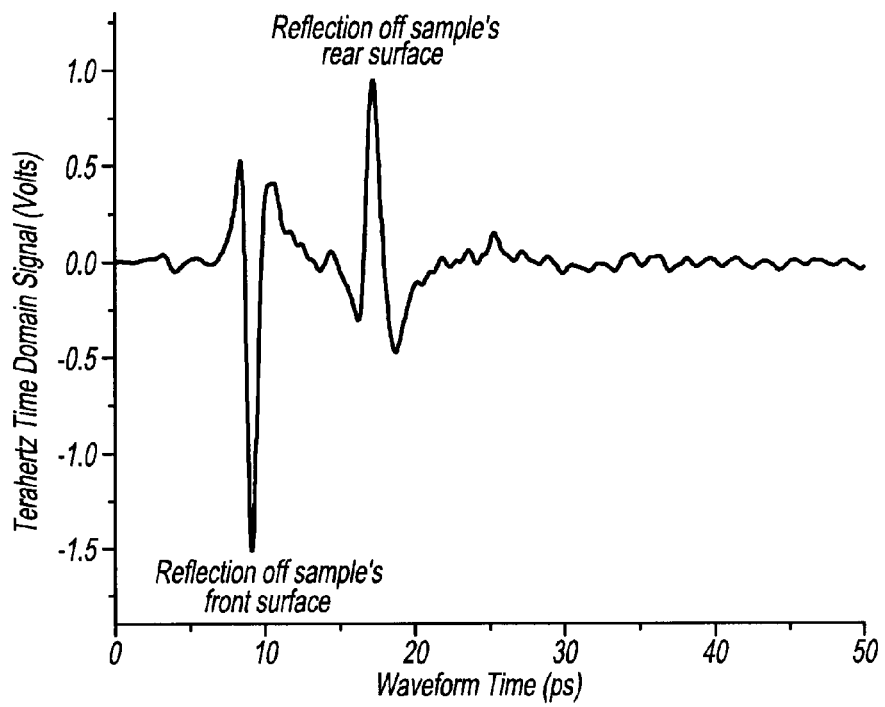
FIG. 6 illustrates a reflection TD-THz waveform from a sample.

The thickness of the etalon would be varied to provide the best calibration precision. Ideally, the etalon would only reflect a small portion of the THz pulse, leaving the bulk of the pulse energy to pass on to the sample. If the etalon were relatively thick, then two cleanly separated reflection peaks (as seen in FIG. 6 and FIG. 22) would result. Then a measure of the delta time between the two calibration etalon peaks would be the preferred time analysis method. If the etalon were sufficiently thin, it would reflect less THz energy, which is preferred. However, in this case the individual interfaces would not be time resolved and the model fit using amplitude fit method discussed earlier would be required. Which method and algorithm provides better sample measurement precision would depend on the sample and experimental conditions (e.g., measurement rate).

Figure 34:
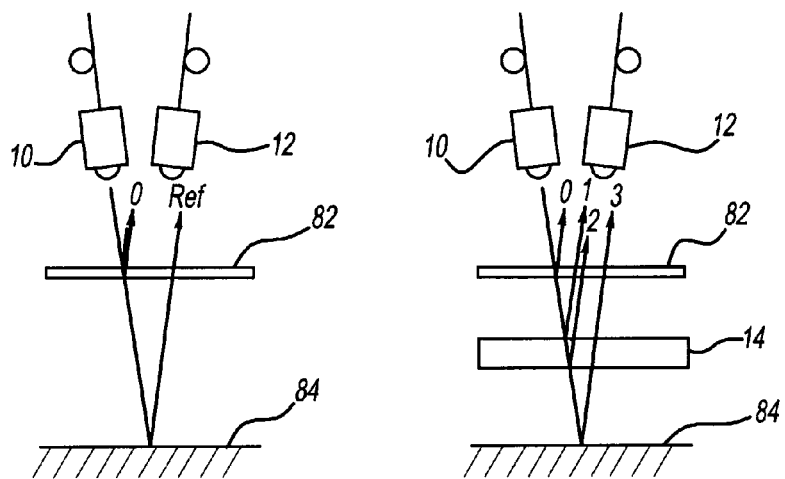
FIG. 34 illustrates a ICE/Rear Reflector Structure, wherein the left most figure is an empty structure, while the right most figure is the structure with a sample.

As shown in FIG. 34, the use of a rear reflector 82 with the Internal Calibration Etalon (ICE) 84 allows improved measurement precision of other sample properties. An example is the absolute thickness of the sample. The typical method to calculate the thickness of a sample requires the value of the delta pulse transit times for the TD-THz pulse reflections off the front and rear surfaces of the sample and knowledge of the sample's refractive index. With the use of an ICE and rear reflector, higher precision thickness measurements can be made without knowledge of the sample material's refractive index.

For this method, the delta pulse transit time value for the empty structure needs to be measured and recorded. This value is used in the calculation of the absolute sample thickness.

Once the sample is inserted in the structure, at least four pulses are observed (FIG. 35). Using the high precision methods discussed above, the transit times ($T_{pk\#}$) for all the pulses needs to be found.

With these high precision values, the absolute thickness of the sample can be calculated according to the following formula:

$$\text{Thickness} = (T_{Ref} - T_{Pk1} - T_{Pk3} - T_{Pk2}) \times c$$

All $T_{Pk}$ times are relative to the $T_{Pk0}$ time. The $T_{Ref}$ value is measured with the empty ICE/Rear Reflector structure. c is the known value for the speed of light. The calculation provides high precision result for the sample thickness regardless of the sample material composition.

Figure 1:
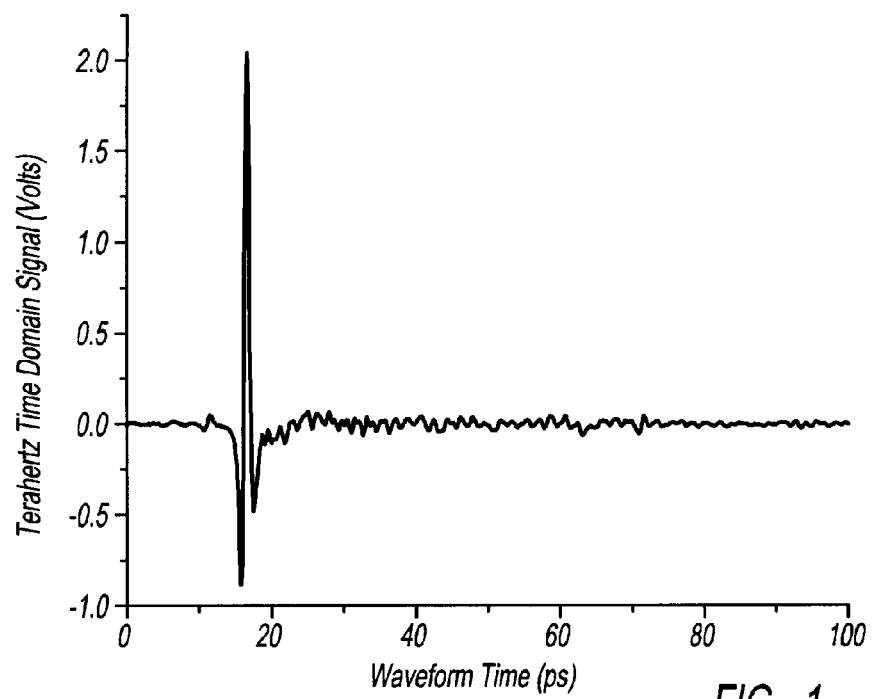
FIG. 1 illustrates a Time-Domain Terahertz (TD-THz) Waveform.
Figure 4:
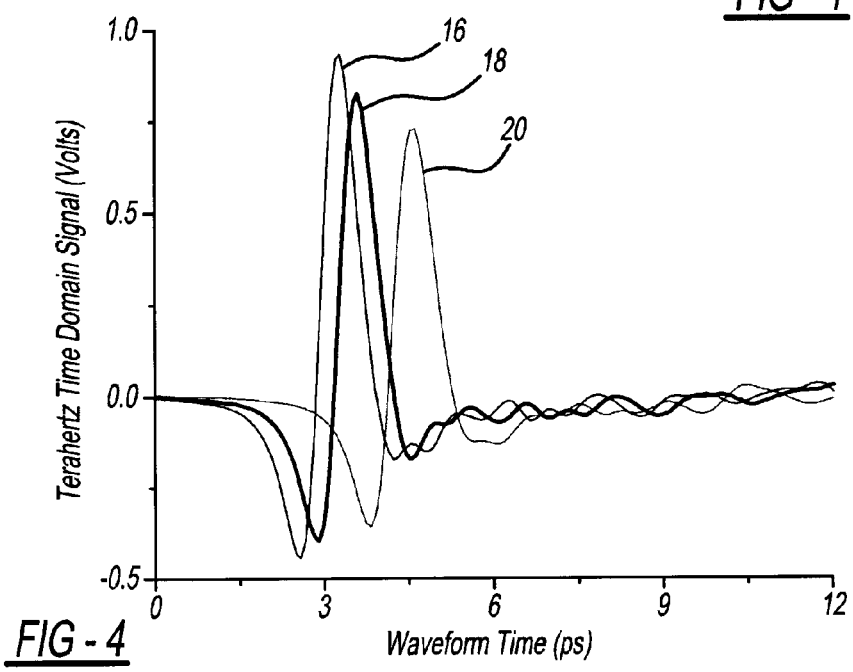
FIG. 4 illustrates a transmission measurement of air and various thickness samples.
Figure 3:
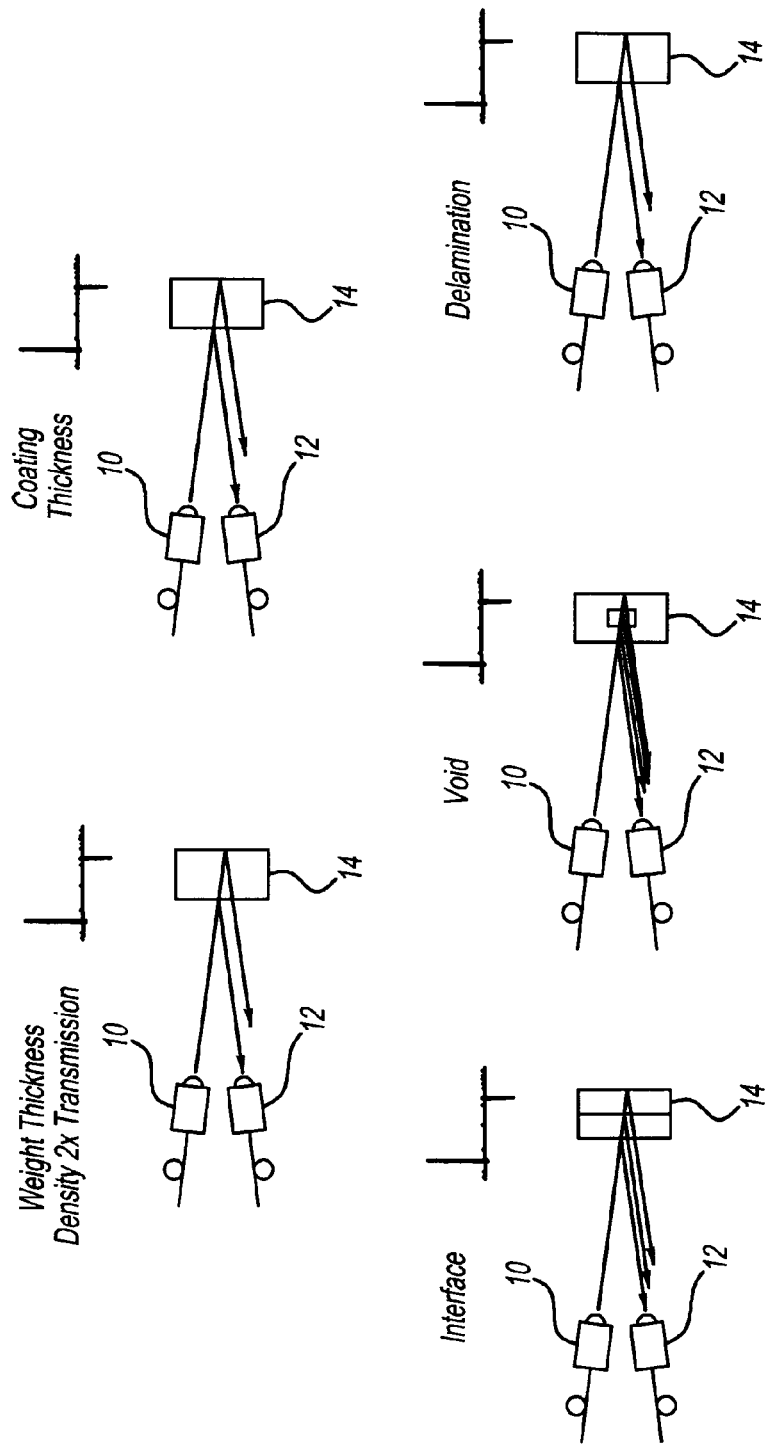
FIG. 3 illustrates a Example Reflection Interactions of TD-THz pulses.
Figure 5:
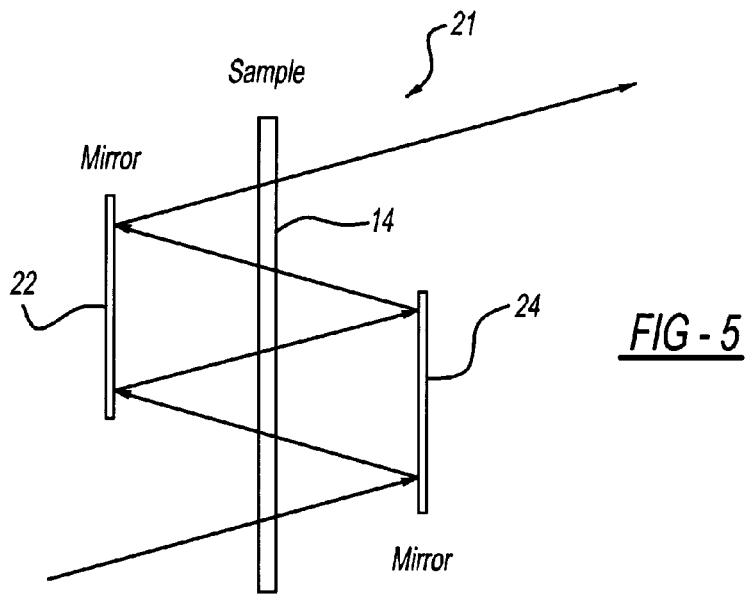
FIG. 5 illustrates a multipass sample chamber.

As illustrated in FIG. 4, multipassing the THz pulse through the sample in a transmission measurement would increase the observed time-of-flight delay between an air reference and sample scan without increasing the imprecision of the timing measurement. This is desirable.

However, an undesirable aspect of transmission measurements is changes in the air reference scan (e.g., drift) or in the THz transmitter/receiver spacing (e.g., mechanical motion) are in general indistinguishable from changes in the sample. The follow system and method addresses this issue.

Referring to FIG. 36, a first multipass sample chamber 86 with a sample 14 and a second multipass sample chamber 88 without a sample are shown. The first and second multipass sample chambers 86 and 88 each include a fully reflecting mirrors 90 and 92 and partially reflecting mirrors 94 and 96. Also shown are resulting sample waveforms 98 and 100 for the multipass sample chambers 86 and 88, respectively. If one side of the multipass sample chambers 86 and 88 were selected to be only partially reflecting, then multiple acquisitions of the transmitting THz pulse are possible within the same time-domain waveform.

The thickness of the sample would be determined by the increase in the spacing between transmission pulses for the sample compared to air. Thus, the pulse delta time value for air would be a required value. However this valve would be relatively easy to measure as the delta time would be determined by the sample multipass etalon spacing. This spacing could be set to any appropriate distance to give clear separation between the transmission pulses. This minimum separation would be maintained for all sample thicknesses, that is the two pulse do not convolve and interfere with each other as is seen for reflection measurement of thin sample. This aspect would be quite advantageous for transmission measurements. Additionally, the advantage of the multiple transmissions passes increasing the measured time-of-flight delay (as a multiple of the number of pass through the sample) still exists. That is the delay between the first and third transmission pulses would be four times that of an air/single pass transmission. This will translate into significantly improved precision of the delta time measurement.

Another improvement can be realized because the mechanical stability effect on the measurement would only depend on the etalon spacing, rather than the transmitter to receiver distance. It will be easier to choose materials and construction methods for the etalon that will produce greater thermal and mechanical stability. Improvements in the sample chamber etalon stability will directly translate into improved precision of the measurement.

Figure 37:
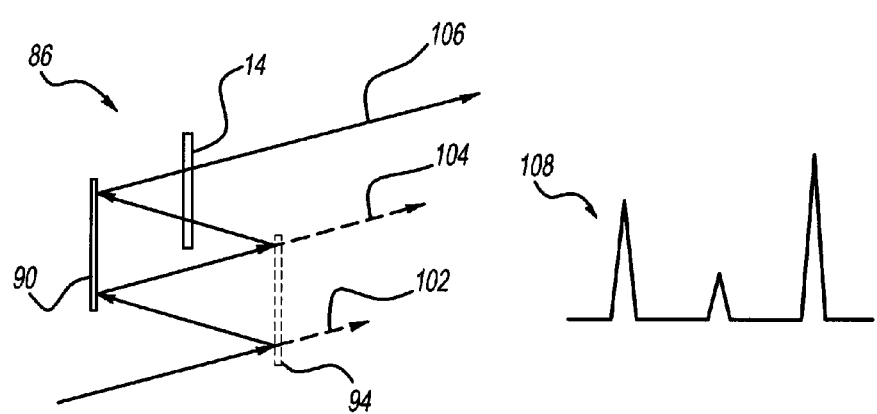
FIG. 37 illustrates a multipass sample etalon chamber with a simultaneous reference air path.

FIG. 37 shows another embodiment of the multipass sample chamber 86, which shows a first transmission pulse 102, a second transmission pulse 104 and a third transmission pulse 106. If it is possible to increase the etalon such that a set pulse etalon reflections occurs with no sample in the THz beam, then the resulting waveform will simultaneously provide information of the etalon and the increase in time-of-flight for the transmission pulse through the sample. FIG. 37 also illustrates the resulting waveform 108.

Figure 38:
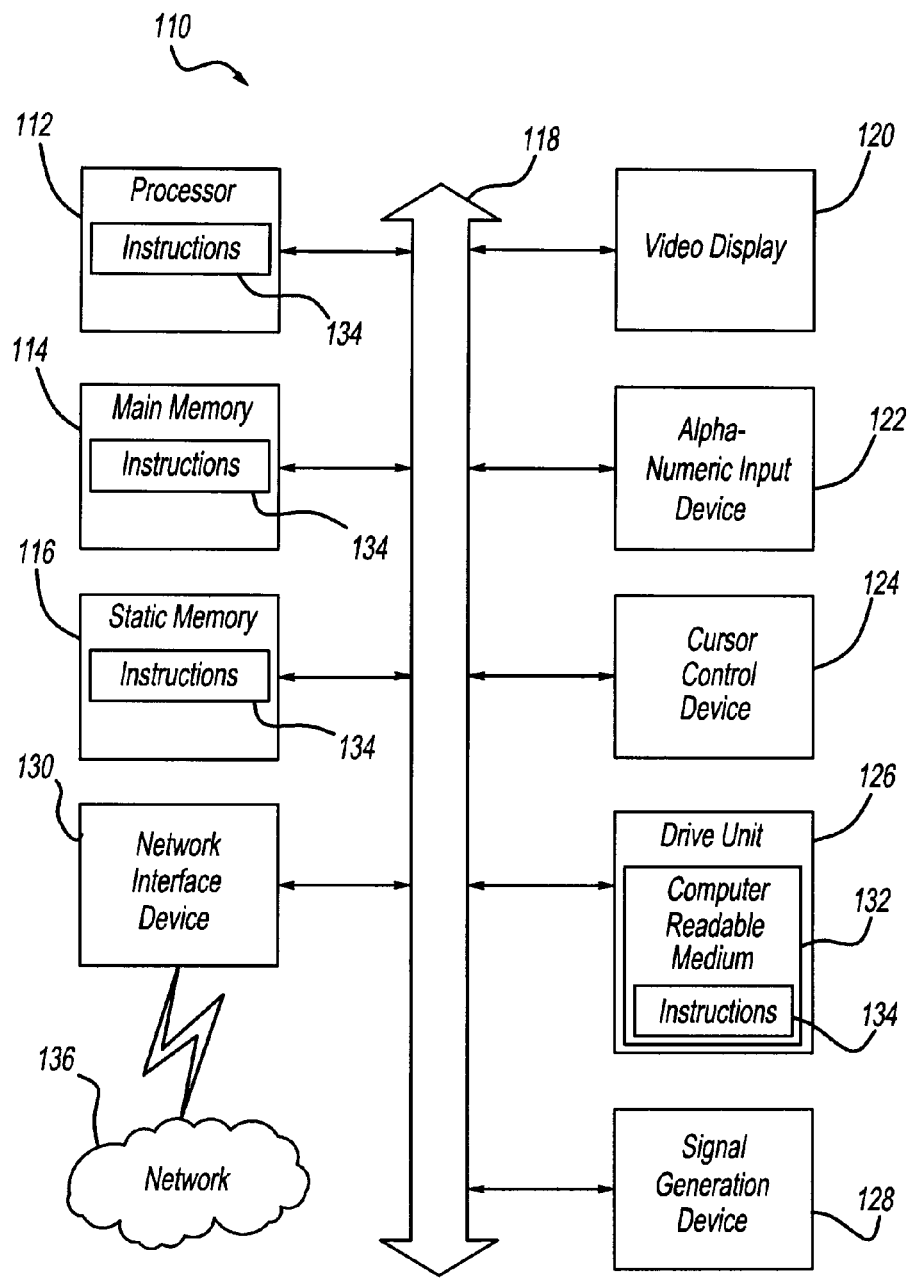
FIG. 38 is a block diagram of a general purpose computer embodying the principles of the present invention.

Referring to FIG. 38, an illustrative embodiment of a general computer system is shown and is designated 110. The computer system 110 can include a set of instructions that can be executed to cause the computer system 110 to perform any one or more of the methods or computer based functions disclosed herein. computer system 110 may operate as a standalone device or may be connected, e.g., using a network, to other computer systems or peripheral devices.

In a networked deployment, the computer system may operate in the capacity of a server or as a client user computer in a server-client user network environment, or as a peer computer system in a peer-to-peer (or distributed) network environment. The computer system 110 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular embodiment, the computer system 110 can be implemented using electronic devices that provide voice, video or data communication. Further, while a single computer system 80 is illustrated, the term "system" shall also be taken to include any collection of systems or sub-systems that individually or jointly execute a set, or multiple sets, of instructions to perform one or more computer functions.

As illustrated in FIG. 38, the computer system 110 may include a processor 112, e.g., a central processing unit (CPU), a graphics processing unit (GPU), or both. Moreover, the computer system 110 can include a main memory 114 and a static memory 116 that can communicate with each other via a bus 118. As shown, the computer system 110 may further include a video display unit 120, such as a liquid crystal display (LCD), an organic light emitting diode (OLED), a flat panel display, a solid state display, or a cathode ray tube (CRT). Additionally, the computer system 110 may include an input device 122, such as a keyboard, and a cursor control device 124, such as a mouse. The computer system 110 can also include a disk drive unit 126, a signal generation device 128, such as a speaker or remote control, and a network interface device 130.

In a particular embodiment, as depicted in FIG. 28, the disk drive unit 126 may include a computer-readable medium 132 in which one or more sets of instructions 134, e.g. software, can be embedded. Further, the instructions 134 may embody one or more of the methods or logic as described herein. In a particular embodiment, the instructions 134 may reside completely, or at least partially, within the main memory 114, the static memory 116, and/or within the processor 112 during execution by the computer system 110. The main memory 114 and the processor 82 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

The present disclosure contemplates a computer-readable medium that includes instructions 134 or receives and executes instructions 134 responsive to a propagated signal, so that a device connected to a network 136 can communicate voice, video or data over the network 136. Further, the instructions 134 may be transmitted or received over the network 136 via the network interface device 130.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

In the Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A system for interpreting a terahertz waveform, the system comprising:
    a terahertz transmitter configured to output a pulse of terahertz radiation;
    a terahertz receiver configured to receive at least a portion of the pulse of terahertz radiation;
    a first optical interface providing optical interference to the pulse of terahertz radiation, wherein the first optical interface will reflect a first optical interface reflected portion of the pulse of terahertz radiation to the terahertz receiver;
    a second optical interface providing optical interference to the pulse of terahertz radiation, wherein the second optical interface will reflect a second optical interface reflected portion of the pulse of terahertz radiation to the terahertz receiver;
    an etalon spacing being defined between the first optical interface and the second optical interface, the etalon spacing being configured to receive a sample to be irradiated by the pulse of terahertz radiation; and
    wherein the sample will reflect a first sample reflected portion of the pulse of terahertz radiation to the terahertz receiver and a second sample reflected portion of the pulse of terahertz radiation to the terahertz receiver.

2. The system of claim 1, wherein the etalon spacing is fixed.

3. The system of claim 1, wherein the etalon spacing is a measurable distance.

4. The system of claim 1, wherein the terahertz receiver is configured to electronically output to a data acquisition system time domain terahertz waveforms, the time domain terahertz waveforms comprising the first optical interface reflected portion, the second optical interface reflected portion, the first sample reflected portion, and the second sample reflected portion.

5. The system of claim 4, wherein the data acquisition system comprises a processor configured to
    select either a peak to peak analysis method, an edge midpoint analysis method, deconvolution analysis method, a model fitting analysis method or a combination of the deconvolution analysis method and a model fitting analysis method for interpreting the at least one time domain terahertz waveform.

6. The system of claim 5, wherein during the peak to peak analysis method, the processor is configured to:
    find a maximum amplitude of at least one time domain terahertz waveform;
    find a minimum amplitude of the at least one time domain terahertz waveform;

determine a difference between the a maximum amplitude of the at least one time domain terahertz waveform and the minimum amplitude of the at least one time domain terahertz waveform;

wherein the amplitude difference correlates to a time delay as the pulse of terahertz radiation travels though the sample; and wherein the time delay correlates to the thickness of the sample.

7. The system of claim 5, wherein during the edge midpoint analysis method, the processor is configured to:
find a maximum amplitude point of at least one time domain terahertz waveform;
find a minimum amplitude point of the at least one time domain terahertz waveform;
determine which of the maximum amplitude point and minimum amplitude point occurred first with respect to time;
when the minimum amplitude point occurred first with respect to time, finding the minimum amplitude point of the at least one time domain terahertz waveform by stepping back with respect to time along the at least one time domain terahertz waveform from the maximum amplitude point;
when the maximum amplitude point occurred first with respect to time, finding the maximum amplitude point of the at least one time domain terahertz waveform by stepping back with respect to time along the at least one time domain terahertz waveform from the minimum amplitude point;
utilizing linear regression between the minimum amplitude point and the maximum amplitude point to calculate a best fit line between the minimum amplitude point and the maximum amplitude point; and
wherein a pulse time of the at least one time domain terahertz waveform is the midpoint of best fit line between the minimum amplitude point and the maximum amplitude point.

8. The system of claim 5, wherein during the deconvolution analysis the processor is configured to deconvolve and filter at least one time domain terahertz waveform using a reference waveform to create a deconvolved time domain terahertz waveform.

9. The system of claim 8, wherein the reference waveform comprises a waveform reflected from a single interference.

10. The system of claim 9, wherein the reference waveform is modified to account for other factors such as optical interference.

11. The system of claim 8, wherein the processor is further configured to:
identify the maxima and the minima of the deconvolved filtered waveform;
provide a reference deconvolved filtered waveform; and
best fit the reference deconvolved filtered waveform to at least one feature of the deconvolved filtered waveform to output a time and amplitude of a peak in the deconvolved filtered waveform.

12. The system of claim 11, wherein the best fit step utilizes a simplex method.

13. The system of claim 5, wherein during the model fitting analysis, the processor is configured to:
identify the maxima and the minima of at least one time domain terahertz waveform;
provide a reference time domain terahertz waveform; and
best fit the reference time domain terahertz waveform to at least one feature of the at least one time domain terahertz waveform to output a time and amplitude of a peak in the time domain terahertz waveform.

14. The system of claim 13, wherein the best fit step utilizes a simplex method.

15. The system of claim 1, wherein a portion of the pulse of terahertz radiation passes more than once through the sample.

16. A system for interpreting a terahertz waveform, the system comprising:
a terahertz transmitter configured to output a pulse of terahertz radiation;
a terahertz receiver configured to receive at least a portion of the pulse of terahertz radiation;
an optical interface providing optical interference to the pulse of terahertz radiation, wherein the optical interface will reflect an optical interface reflected portion of the pulse of terahertz radiation to the terahertz receiver;
wherein the sample will reflect a first sample reflected portion of the pulse of terahertz radiation to the terahertz receiver and a second sample reflected portion of the pulse of terahertz radiation to the terahertz receiver; and
wherein the optical interface is located between the terahertz transmitter and the sample.

17. The system of claim 16, wherein the terahertz receiver is configured to electronically output to a data acquisition system time domain terahertz waveforms, the time domain terahertz waveforms comprising the optical interface reflected portion, the first sample reflected portion, and the second sample reflected portion.

18. The system of claim 17, wherein the data acquisition system comprises a processor configured to select either a peak to peak analysis method, an edge midpoint analysis method, deconvolution analysis method, a model fitting analysis method or a combination of the deconvolution analysis method and a model fitting analysis method for interpreting the at least one time domain terahertz waveform.

19. The system of claim 18, wherein during the peak to peak analysis method, the processor is configured to:
find a maximum amplitude of at least one time domain terahertz waveform;
find a minimum amplitude of the at least one time domain terahertz waveform;
determine a difference between the a maximum amplitude of the at least one time domain terahertz waveform and the minimum amplitude of the at least one time domain terahertz waveform;
wherein the amplitude difference correlates to a time delay as the pulse of terahertz radiation travels though the sample; and
wherein the time delay correlates to the thickness of the sample.

20. The system of claim 18, wherein during the edge midpoint analysis method, the processor is configured to:
find a maximum amplitude point of at least one time domain terahertz waveform;
find a minimum amplitude point of the at least one time domain terahertz waveform;
determine which of the maximum amplitude point and minimum amplitude point occurred first with respect to time;
when the minimum amplitude point occurred first with respect to time, finding the minimum amplitude point of the at least one time domain terahertz waveform by stepping back with respect to time along the at least one time domain terahertz waveform from the maximum amplitude point;
when the maximum amplitude point occurred first with respect to time, finding the maximum amplitude point of the at least one time domain terahertz waveform by stepping back with respect to time along the at least one time domain terahertz waveform from the minimum amplitude point;

utilizing linear regression between the minimum amplitude point and the maximum amplitude point to calculate a best fit line between the minimum amplitude point and the maximum amplitude point; and wherein a pulse time of the at least one time domain terahertz waveform is the midpoint of best fit line between the minimum amplitude point and the maximum amplitude point.

21. The system of claim 18, wherein during the deconvolution analysis the processor is configured to deconvolve and filter at least one time domain terahertz waveform using a reference waveform to create a deconvolved time domain terahertz waveform.

22. The system of claim 21, wherein the reference waveform comprises a waveform reflected from a single interference.

23. The system of claim 22, wherein the reference waveform is modified to account for other factors such as optical interference.

24. The system of claim 22, wherein the processor is further configured to:
identify the maxima and the minima of the deconvolved filtered waveform;
provide a reference deconvolved filtered waveform; and
best fit the reference deconvolved filtered waveform to at least one feature of the deconvolved filtered waveform to output a time and amplitude of a peak in the deconvolved filtered waveform.

25. The system of claim 24, wherein the best fit step utilizes a simplex method.

26. The system of claim 18, wherein during the model fitting analysis, the processor is configured to:
identify the maxima and the minima of at least one time domain terahertz waveform;
provide a reference time domain terahertz waveform; and
best fit the reference time domain terahertz waveform to at least one feature of the at least one time domain terahertz waveform to output a time and amplitude of a peak in the time domain terahertz waveform.

27. The system of claim 16, wherein a portion of the pulse of terahertz radiation passes more than once thought the sample.

* * * * *

UNITED STATES PATENT AND TRADEMARK OFFICE
CERTIFICATE OF CORRECTION

PATENT NO. : 8,457,915 B2  Page 1 of 1
APPLICATION NO. : 12/667986
DATED : June 4, 2013
INVENTOR(S) : White et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 541 days.

Signed and Sealed this
Eighth Day of September, 2015

Michelle K. Lee
*Director of the United States Patent and Trademark Office*